(12) United States Patent  
Yamakawa

(10) Patent No.: US 6,285,028 B1
(45) Date of Patent: Sep. 4, 2001

(54) SEMICONDUCTOR RADIATION DETECTOR AND NUCLEAR MEDICINE DIAGNOSTIC APPARATUS

(75) Inventor: Tsutomu Yamakawa, Nasu-gun (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/322,991

(22) Filed: Jun. 1, 1999

(30) Foreign Application Priority Data

Jun. 2, 1998 (JP) .................................................. 10-152945
Jan. 11, 1999 (JP) .................................................. 11-004529
Jan. 29, 1999 (JP) .................................................. 11-022912

(51) Int. Cl.$^7$ ........................................................ G01T 1/24
(52) U.S. Cl. .................................. 250/370.09; 250/370.1
(58) Field of Search ........................... 250/370.09, 370.01, 250/370.07, 370.1; 378/4, 98.8

(56) References Cited

U.S. PATENT DOCUMENTS

| 4,879,464 | * | 11/1989 | Iinuma ............................ | 250/361 R |
| 4,931,648 | * | 6/1990 | Elliott et al. ...................... | 250/370.1 |
| 5,434,417 | * | 7/1995 | Nygren ............................ | 250/370.01 |
| 5,585,638 | * | 12/1996 | Hoffman ......................... | 250/370.07 |
| 5,753,921 | * | 5/1998 | Trauernicht et al. ............ | 250/370.09 |
| 5,786,597 | * | 7/1998 | Lingren et al. ................... | 250/370.9 |

OTHER PUBLICATIONS

0039–7149–2S, U.S. application No. 09/277,162, filed Mar. 26, 1999, pending.

* cited by examiner

Primary Examiner—Robert H. Kim
Assistant Examiner—Irakli Kiknadze
(74) Attorney, Agent, or Firm—Oblon, Spivak, McClelland, Maier & Neustadt, P.C.

(57) ABSTRACT

A semiconductor radiation detector has a plurality of semiconductor cells for detecting radiation from a subject. These semiconductor cells include a plurality of voltage application electrodes and a plurality of signal read electrodes. The semiconductor cells are so arrayed that the cell array forms a concave shape and the semiconductor cells are parallel to each other. Since the semiconductor cells are arrayed to form a concave shape, not only semiconductor cells near the center but also semiconductor cells near the peripheries are located close to the subject. This increases the positional resolution and sensitivity. Since the semiconductor cells are arranged parallel to each other, collimated gamma rays always perpendicularly enter the incidence surface regardless of the incident position of the gamma rays. This equalizes the distances the gamma rays travel regardless of the incident positions, so the sensitivity is substantially constant regardless of the incident positions.

29 Claims, 14 Drawing Sheets

SEMICONDUCTOR RADIATION DETECTOR AND NUCLEAR MEDICINE DIAGNOSTIC APPARATUS

BACKGROUND OF THE INVENTION

The present invention relates to a multi-channel semiconductor radiation detector for detecting radiation (gamma rays) emitted from radioactive isotopes (radioisotopes, RIS) injected into a subject such as a patient, and a nuclear medicine diagnostic apparatus for generating the RI distribution in the body on the basis of the detection result.

A nuclear medicine diagnostic apparatus can detect radiation such as gamma rays emitted from a subject into which RIs are injected, and obtain the RI distribution in the body on the basis of the detection result. With this RI distribution, fundamental data of functional diagnoses, e.g., identification of a morbid portion in the body and measurements of the blood flow rate and the fatty acid metabolic amount can be acquired.

As this nuclear medicine diagnostic apparatus, a SPECT apparatus using single photon emission computer tomography (SPECT) and a PET apparatus using coincidence detection type positron emission computer tomography (PET) are known. The latter PET apparatus includes a plurality of detectors and performs imaging by simultaneously detecting gamma rays emitted at an angle of 180° when positrons combine with electrons and disappear.

Recently, a SPECT apparatus which includes a plurality of detectors to perform both the SPECT and the coincidence detection type PET is becoming popular. A "nuclear medicine diagnostic apparatus" is a general term for these apparatuses.

As a detector of the conventional SPECT apparatuses, an Anger type detector in which a plurality of photomultiplier tubes are densely arranged on a scintillator is used most frequently. However, this Anger type detector is large and has relatively low energy resolution and detection characteristics.

A prevalent method used in the coincidence detection type PET apparatus is to perform imaging by simultaneously detecting the timings at which gamma rays are emitted at an angle of 180° by using the combination of a bismuth germanium oxide (BGO) detector and a photomultiplier or a photodiode.

Also, a nuclear medicine diagnostic apparatus which uses an Anger type detector having a plurality of detectors and can realize the coincidence detection type PET by mode switching is currently put to use in many cases.

In any nuclear medicine diagnostic apparatus, however, a detector for detecting gamma rays is a scintillator type detector. So, it is necessary to once convert incident gamma rays into weak light by the scintillator and convert this weak light into an electrical signal by a photomultiplier tube or the like. This increases the size of a nuclear medicine diagnostic apparatus and limits its performance.

A semiconductor radiation detector, therefore, is attracting attention. Since a semiconductor radiation detector converts gamma rays directly into an electrical signal, the efficiency of conversion to an electrical signal is high. Additionally, semiconductor detecting elements can individually detect gamma rays. Hence, a semiconductor radiation detector is expected to improve the energy resolution and detection characteristics.

A cadmium telluride (CdTe) semiconductor cannot form a single-crystal structure such as formed by sodium iodide (NaI) used in the present Anger type detector. In one prior art, therefore, a two-dimensional semiconductor radiation detector is constructed by densely mounting small detector modules (incorporating a two-dimensional semiconductor array cell and a preamplifier and read circuit formed below this two-dimensional array cell so as not to extend from the cell). Unfortunately, interconnections between these detector modules and dead spaces inside the detector modules are nonuniform, and a unique artifact occurs. This makes reconstruction of RI images difficult.

Additionally, a modular construction like this can perform only signal processing each detector module is capable of. Therefore, signal processing is presently very difficult when coincidence detection is observed over a plurality of semiconductor detecting elements (i.e., a plurality of detector modules) in a nuclear medicine diagnostic apparatus, such as the coincidence detection type PET apparatus, which processes a high energy of 511 kev.

Also, it is difficult to form fine pixels such as in a conventional digital gamma camera by using semiconductor detecting elements used in a semiconductor radiation detector due to restrictions on the cost and packaging method. This limits the formation of fine structures.

The Anger type detector is generally designed as a plane detector. As shown in FIG. 1, an Anger type plane detector has a plane parallel collimator 10 and a plane scintillator 11. An RI injected into a subject P emits gamma rays from inside the body of the subject P, and the scintillator 11 converts the gamma rays into light via the parallel collimator 10. This light is converted into an electrical signal by, e.g., a photomultiplier tube (not shown) and subjected to signal processing. The subject P has a curved surface. Therefore, although the center of the Anger type plane detector shown in FIG. 1 is close to the subject P, this plane detector separates from the subject P toward the periphery of the subject P. Consequently, the positional resolution pertaining to detection of the incident position of gamma rays generally deteriorates.

Instead of this Anger type plane detector, a detector having curved surfaces which allow the whole detector to be located close to a patient can be used. As shown in FIG. 2, this Anger type gamma camera (manufactured by BICRON Corp.) includes two concave curved detectors 20a and 20b opposing each other with a subject P between them. These curved detectors 20a and 20b are separated by a rotation radius R from a rotation center O and moved around the subject P along a rotating direction D1 by a driving mechanism (not shown).

The curved detectors 20a and 20b have the same arrangement; the curved detector 20a includes a scintillator 21a, a light guide 22a, and photomultiplier tubes 23a to 23n, and the curved detector 20b includes a scintillator 21b, a light guide 22b, and photomultiplier tubes 24a to 24n. Each of the scintillators 21a and 21b is a concave cylindrical member and has a fixed thickness t1 in a direction to the rotation center O. The photomultiplier tubes 23a to 23n and 24a to 24n opposing the rotation center O detect the incident position of gamma rays.

In the curved detector 20a or 20b with the above construction, the accurate incident positions of gamma rays entering the center and vicinity of the scintillator 21a or 21b can be calculated by using the photomultiplier tubes because there is no big difference between the incident positions. However, if parallel collimators (not shown) are set on the subject sides of the scintillators 21a and 21b to detect parallel gamma rays in the SPECT, the distance the gamma rays travel through the scintillator 21a or 21b increases from the center to the peripheries of the curved detector 20a or 20b. This is so because the scintillators 21a and 21b have the thickness t1 in the form of a cylinder in the direction to the rotation center O.

Accordingly, the influence of DOI (Depth Of Interaction) increases, and this produces a positional resolution error Δ in accordance with the position where the scintillator 21a or 21b absorbs gamma rays. Consequently, the accuracy of calculated positional resolution deteriorates. Although the peripheries of the curved detectors 20a and 20b are located close to the subject P, the positional resolution does not increase. This prevents the SPECT from fully utilizing the merit that the peripheries of the detector are closely located to a subject. Additionally, the sensitivity changes in accordance with the incident position of gamma rays (the sensitivity rises toward the peripheries). Hence, it is difficult to increase the sensitivity in the center, which is originally preferably high.

In the coincidence detection type PET, the position of a positron PO (511 keV) along a line extending perpendicularly to the curved surfaces of the scintillators 21a and 21b from the rotation center O is ideally calculable. However, when parallel gamma rays are detected by using parallel collimators as described above, the distance the gamma rays from the positron PO travel through the scintillator 21a or 21b increases toward the peripheries to increase the influence of DOI, because the scintillators 21a and 21b have the fixed thickness t1 in the form of a cylinder in the direction to the rotation center O. Since this deteriorates the positional resolution, the quality of a reconstructed RI image deteriorates.

Especially when the thickness t1 of the scintillators 21a and 21b is large, an incident position where the influence of DOI is conspicuous exists depending on the incident angle of gamma rays from the positron PO. For this reason, when a gamma camera in which two detectors oppose each other is used, satisfactory image quality can be obtained only when these two detectors are separated a predetermined distance or more, because a coincidence detection solid angle θ1 becomes small. Accordingly, although a curved detector originally has the merit that its solid angle is larger than that of a plane detector, the coincidence detection solid angle θ1 for gamma ray detection in the PET cannot be increased more than expected of a curved detector. As a consequence, the sensitivity cannot unlimitedly increase.

Additionally, for the reasons described earlier, the positional resolution largely deteriorates in the peripheries of a detector even in the fan beam SPECT in which the focal length is short.

Furthermore, when the simultaneous use of the SPECT and the coincidence detection type PET is desirable, it is difficult to perform these two methods at the same time and obtain a greater merit than when a plane detector is used.

Also, as described above, the scintillator has a fixed thickness in the form of a cylinder in the direction to the rotation center 0. Therefore, when parallel gamma rays are detected by using parallel collimators, the sensitivity changes in accordance with the incident position of the gamma rays (the sensitivity rises toward the peripheries). Consequently, it is difficult to increase the sensitivity in the center of the detector, which is originally preferably high.

Moreover, to acquire projection data concerning cardiac muscles over an angle of 180° by using the Anger type plane detector, there is a method by which two plane detectors are separated by an angle of 90° and the whole detector assembly is rotated 90°. Since, however, the incident surface of each detector is a plane surface, these incident surfaces cannot approach the heart of a subject more than expected.

BRIEF SUMMARY OF THE INVENTION

It is an object of the present invention to provide a semiconductor radiation detector and nuclear medicine diagnostic apparatus capable of increasing the positional resolution and sensitivity.

A semiconductor radiation detector of the present invention has a plurality of semiconductor cells for detecting radiation from a subject. These semiconductor cells include a plurality of voltage application electrodes and a plurality of signal read electrodes. The semiconductor cells are so arrayed that the cell array forms a concave shape and the semiconductor cells are parallel to each other. Since the semiconductor cells are arrayed to form a concave shape, not only semiconductor cells near the center but also semiconductor cells near the peripheries are located close to the subject. This increases the positional resolution and sensitivity. Since the semiconductor cells are arranged parallel to each other, collimated gamma rays always perpendicularly strike the incidence surface regardless of the incident position of the gamma rays. This equalizes the distances the gamma rays travel regardless of the incident positions, so the sensitivity is substantially constant regardless of the incident positions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
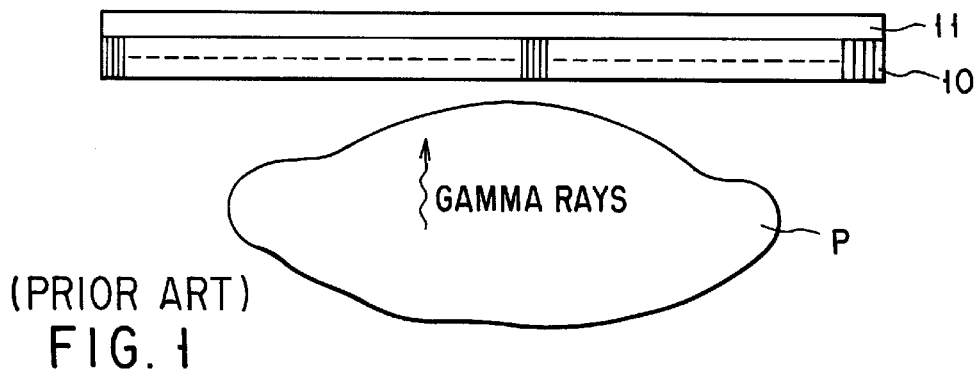
FIG. 1 is a view showing the construction of a conventional Anger type plane detector.
Figure 2:
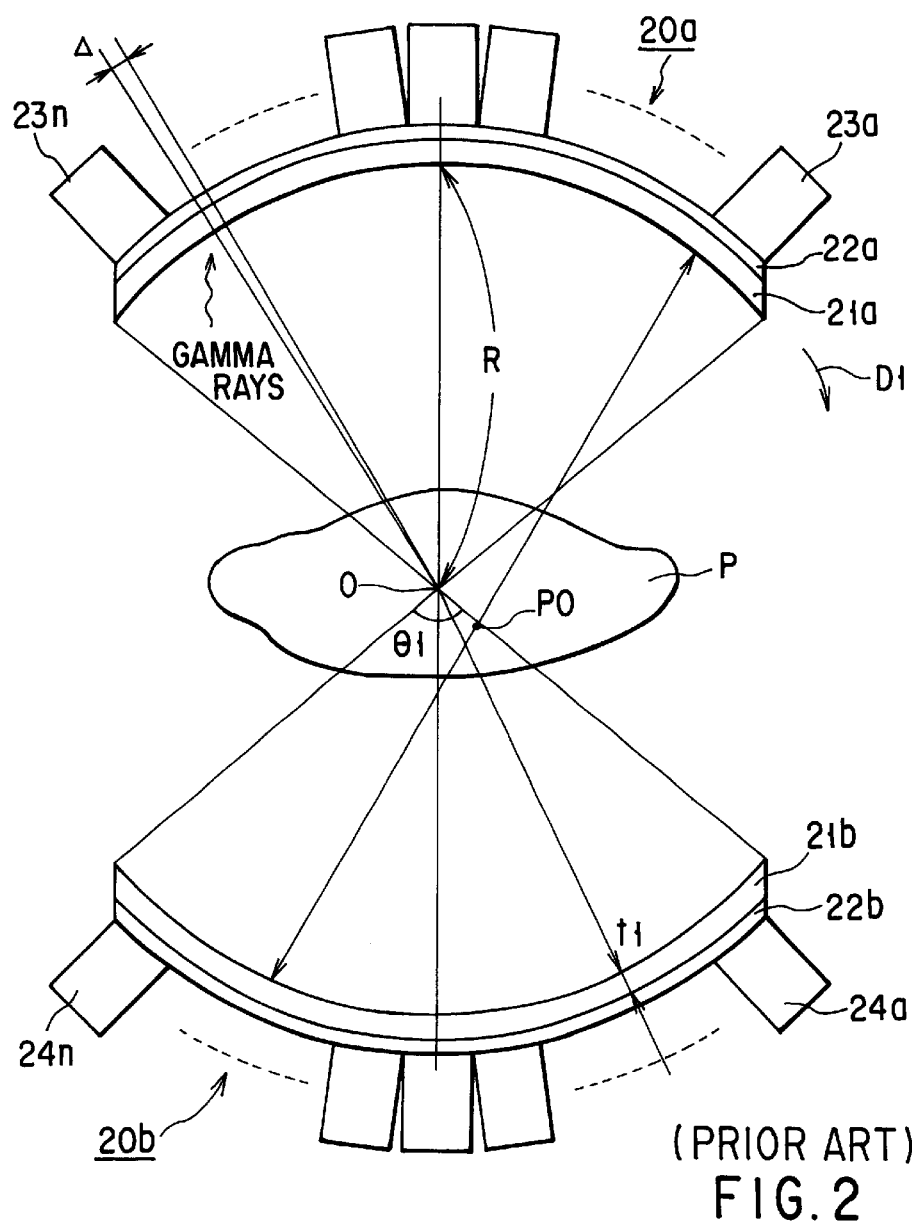
FIG. 2 is a view showing the construction of another conventional Anger type curved detector.
Figure 3:
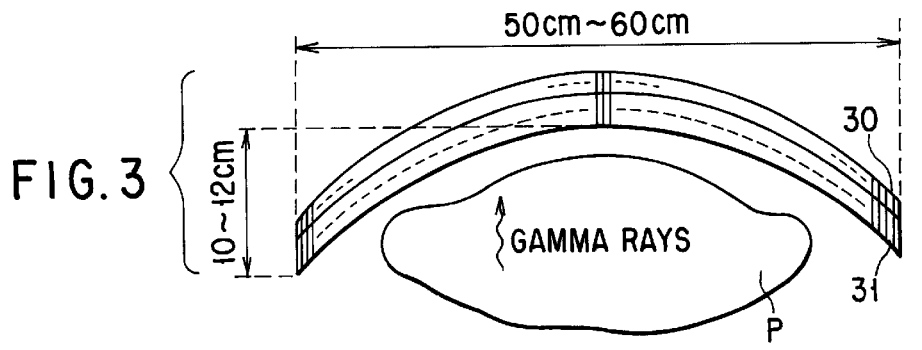
FIG. 3 is a view showing the construction of a semiconductor radiation detector according to a preferred embodiment of the present invention.
Figure 4:
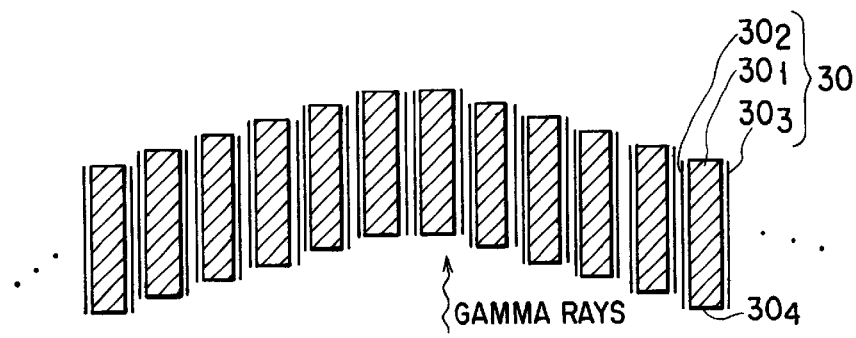
FIG. 4 is an enlarged view of a part of FIG. 3.

A preferred embodiment of the present invention will be described below with reference to the accompanying drawings. FIG. 3 is a view showing the structure of a semiconductor radiation detector according to the preferred embodiment of the present invention. FIG. 4 is an enlarged view of a part of the semiconductor radiation detector shown in FIG. 3.

The semiconductor radiation detector of this embodiment has a plurality of semiconductor detecting elements 30 for detecting radiation (gamma rays) emitted from RIs injected into a subject P. Each of these detecting element 30 includes a prismatic semiconductor cell $30_1$ made of, e.g., CdTe (cadmium telluride), a voltage application electrode $30_2$ adhered to one side surface of the semiconductor cell $30_1$, and a signal read electrode $30_3$ adhered to the opposite side surface of the semiconductor cell $30_1$.

When a voltage (negative voltage) is applied to the voltage application electrode $30_2$, a potential difference is produced between the voltage application electrode $30_2$ and the signal read electrode $30_3$. If gamma rays enter one end face (to be referred to as an incident surface hereinafter) $30_4$ in this state, electrons and holes are generated in the semiconductor cell $30_1$. The generated electrons and holes move to the positive electrode (signal read electrode) $30_3$ and the negative electrode (voltage application electrode) $30_2$, respectively. The resultant induced electric charge is stored in an external charge amplifier via the signal read electrode $30_3$. The charge amplifier outputs an electrical signal proportional to the energy of the incident gamma rays.

This semiconductor detecting element 30 is not restricted to a semiconductor cell type element. For example, the semiconductor detecting element 30 can be the combination of a scintillator and photomultiplier or the combination of a scintillator and photodiode.

The semiconductor cells $30_1$ are so arrayed that the cell array forms a concave shape, the cells are parallel to each other, and the gamma ray incident surfaces $30_4$ face inward. More specifically, the semiconductor cells $30_1$ are so arrayed that the cell array forms the shape of an arch. Additionally, each semiconductor cell $30_1$ slightly projects inward from a neighboring semiconductor cell $30_1$. The amount of this projection changes from one place to another in the array; the projection is shortest in the center of the array and longest in its peripheries. Also, the semiconductor cells $30_1$ are so arrayed that their incident surfaces $30_4$ point in the same direction, i.e., perpendiculars dropped to these incident surfaces $30_4$ are parallel to each other.

To place all the semiconductor cells $30_1$ thus arrayed as close as possible to the subject P and thereby maintain high positional resolution, it is desirable to set the cell array width within the range of 50 to 60 cm and the cell array bent depth within the range of 10 to 12 cm. The cell array curvature can be fixed, or the curvature in the peripheries can be different from that in the center. To cope with various body shapes of the subject P, it is possible to prepare various detectors such as a detector whose peripheral curvature is larger than its central curvature and a detector whose peripheral curvature is smaller than its central curvature, and selectively use these detectors in accordance with the body shape of the subject P.

A collimator 31 having a shape corresponding to the cell array shape is arranged inside the semiconductor cells $30_1$ thus arrayed. This collimator 31 can be any of parallel type, fan beam type, and slant type collimators, and these collimators are interchangeable with respect to the cell array.

A plurality of collimator holes corresponding to the semiconductor cells $30_1$ are formed in the collimator 31. These collimator holes are cylindrical or prismatic. In a parallel type collimator, these collimator holes are so formed that their central axes are parallel to perpendiculars dropped to the incident surfaces $30_4$ of the semiconductor cells $30_1$ and parallel to each other. The collimator 31 with this structure passes only gamma rays entering perpendicularly from the subject P into the incident surfaces $30_4$, and shields gamma rays entering in other directions. In a fan beam type collimator, the collimator holes are so formed that their central axes converge into one point. In a slant type collimator, the collimator holes are so formed that their central axes are parallel to each other and slant to a tangent to the cell array curve.

As described above, the semiconductor cells $30_1$ are arrayed in the form of an arch. Consequently, not only the semiconductor cells $30_1$ near the center but also the semiconductor cells $30_1$ near the peripheries can be placed close to the subject P. This increases the positional resolution and sensitivity.

Also, since the semiconductor cells $30_1$ are arranged parallel to each other, collimated gamma rays always perpendicularly enter the incident surface regardless of the position in the array (the incident position of the gamma rays). This equalizes the distances the gamma rays travel regardless of the position in the array, so the sensitivity is substantially constant regardless of the position in the array.

Recently, a two-dimensional detector is sometimes constructed by densely arranging monolithic module detectors. If this is the case, the semiconductor array as shown in FIG. 3 is difficult to construct.

Figure 5:
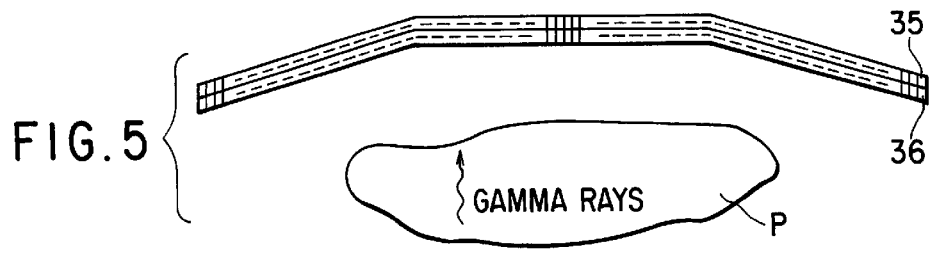
FIG. 5 is a view showing another construction of the semiconductor radiation detector shown in FIG. 3.
Figure 6:
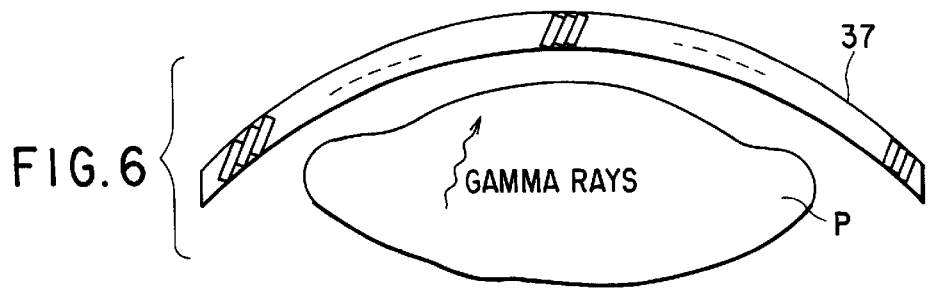
FIG. 6 is a view showing another construction of the nuclear medicine diagnostic apparatus shown in FIG. 3.

This embodiment is not limited to the arched semiconductor radiation detector as shown in FIG. 3. For example, as shown in FIG. 5, a plurality of linear arrays 35 in each of which semiconductor cells $30_1$ are linearly arrayed can be jointed to form the shape of a part of a polygon. In accordance with this structure, a collimator 36 is also formed to have the shape of a part of a polygon. Alternatively, as shown in FIG. 6, semiconductor cells $30_1$ can be slanted to process obliquely incident gamma rays. The incident surfaces of this slant type semiconductor radiation detector 37 can also be placed as close as possible to the subject P. Note that a parallel collimator having collimator holes slanted in the same manner as the semiconductor cells $30_1$ can be mounted near the incident surface of the semiconductor radiation detector 37.

Figure 7:
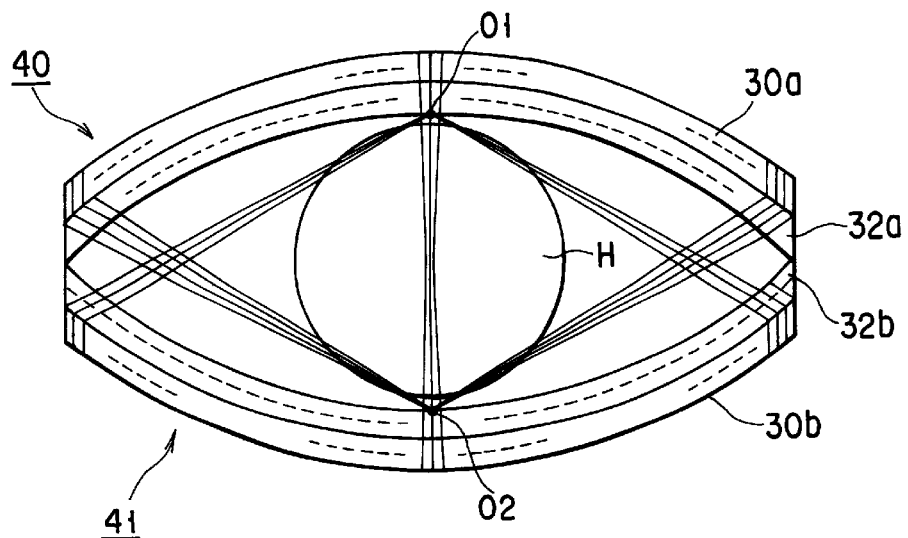
FIG. 7 is a view showing an example of use of this embodiment.

As shown in FIG. 7, fan beam collimators are sometimes set in the aforementioned arched cell array. Two semiconductor radiation detectors 40 and 41, in which fan beam collimators 32a and 32b having a short focal length are set on arched cell arrays 30a and 30b shown in FIG. 3, are installed in positions where these semiconductor radiation detectors 40 and 41 oppose each other with an organ (e.g., a head H) about 20 cm in diameter of a subject P between them. In FIG. 7, reference symbol $O_1$ denotes the focal point of the fan beam collimator 32b; and $O_2$, the focal point of the fan beam collimator 32a.

By using the two semiconductor radiation detectors 40 and 41 in which the fan beam collimators 32a and 32b are set on the arched cell arrays 30a and 30b as described above, it is possible to enlarge the observation field, move the semiconductor radiation detectors closer to the subject P, and increase the coincidence detection solid angle of gamma rays to be detected, none of which is realizable in the conventional Anger type gamma camera fan beam system. Consequently, the quality of a SPECT image of a small-field organ, such as the head H, can be greatly improved.

Also, even when fan beam collimators having a long focal length covering the whole body of the subject P face each other with a long distance between them, it is possible to enlarge the observation field, move the semiconductor radiation detectors closer to the subject, and increase the coincidence detection solid angle of gamma rays to be detected.

So, the quality of a whole-body SPECT image and the like can be improved to be higher than the image quality obtained when semiconductor radiation detectors are simply close to the subject.

As described above, to move the semiconductor cells $30_1$ closer to the subject P regardless of the gamma ray incident position, the width of the observation field of the gamma detectors 40 and 41 is set within the range of 50 to 60 cm and the bent depth of the gamma detectors 40 and 41 is set within the range of 10 to 12 cm. Therefore, even the peripheries of the semiconductor radiation detectors 40 and 41 are close to the subject P, so the positional resolution can greatly improve. Additionally, the semiconductor radiation detectors 40 and 41 can be positioned well close to even a small organ such as the head H.

In FIG. 7, the semiconductor radiation detectors 40 and 41 oppose each other by connecting their end portions. However, the present invention is not limited to this arrangement. For example, the semiconductor radiation detectors can be arranged apart from each other without connecting their end portions. Alternatively, the semiconductor radiation detectors 40 and 41 can be arranged very close to each other without connecting their end portions.

Furthermore, when collimators (not shown) are attached to the incident surfaces of the semiconductor radiation detectors 40 and 41, a cylindrical structure (corresponding to, e.g., the head H of the subject P) having a diameter of at least 24 cm or less (approximately 20 to 24 cm) can be placed in the space formed when the semiconductor radiation detectors 40 and 41 face each other. Accordingly, the shortest distance between the radiation incident surface of the collimator attached to the incident surface of each of the semiconductor radiation detectors 40 and 41 and the surface of this cylindrical structure can be set within the range of 0.5 to 2 cm.

Figure 8:
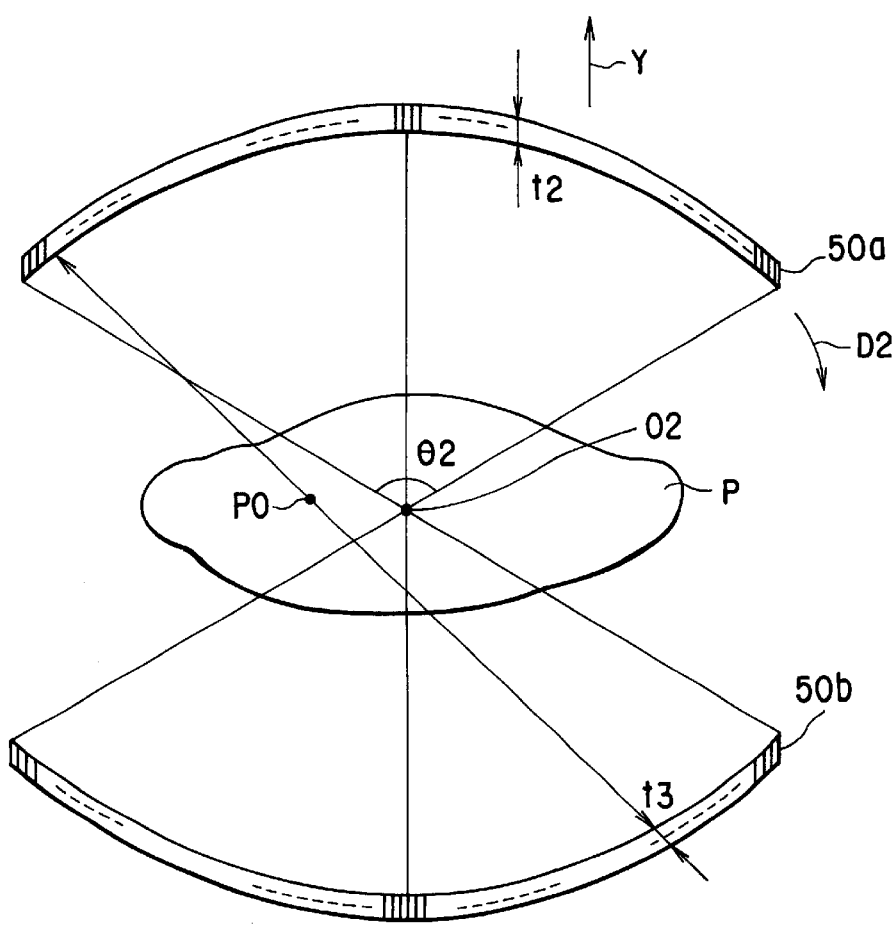
FIG. 8 is a view showing an example of use of this embodiment.

As shown in FIG. 8, cell arrays 50a and 50b face each other with the subject P between them, and a thickness t2 of these cell arrays 50a and 50b is fixed. Therefore, when parallel collimators are set on the cell arrays 50a and 50b to detect parallel gamma rays in the SPECT, the directions (gamma ray absorbing directions) of semiconductor detecting elements in the cell arrays 50a and 50b are the same direction (Y direction). As a result, as in the conventional Anger type detectors, the positional resolution to be calculated does not deteriorate regardless of the incident position. This advantageously improves the positional resolution in the peripheries of the cell arrays 50a and 50b by the reduced distance to the subject P, compared to the conventional Anger type detectors.

Also, as described above, the cell arrays 50a and 50b have the fixed thickness t2 in the Y direction equal to the gamma ray absorbing direction. Hence, a thickness t3 in the direction in which gamma rays entering the cell arrays 50a and 50b in a direction inclined to the Y direction are absorbed is smaller than the thickness t1 of the scintillators of the conventional Anger type detectors. Additionally, a semiconductor radiation detector has a larger absorption coefficient than that of a scintillator made of, e.g., NaI. Therefore, even when gamma rays enter the cell arrays 50a and 50b in a direction inclined to the Y direction, the influence of DOI reduces, and this alleviates deterioration of the positional resolution.

Accordingly, in a coincidence detection type PET apparatus including two detectors facing each other with the subject P between them, the influence of DOI can be relatively reduced even when the semiconductor radiation detectors move around the subject P along a rotating direction D2 while the distance between the detectors is decreased to the extent to which they do not contact the subject P. Also, it is possible not only to increase the coincidence detection solid angle for positrons PO at 511 keV by the use of concave semiconductor radiation detectors but also to increase the coincidence detection solid angle by decreasing the rotation radius of the semiconductor radiation detectors.

Furthermore, even in fan beam SPECT in which the focal length to a small organ such as a head is short, the influence of DOI can be reduced in the same manner as described above, and this alleviates deterioration of the positional resolution.

Additionally, CdTe or cadmium zinc telluride (CZT) semiconductor has a larger absorption coefficient than that of a scintillator made of, e.g., NaI. Therefore, it is possible to further decrease the semiconductor radiation detector thickness and thereby further alleviate the influence of DOI.

Figure 9:
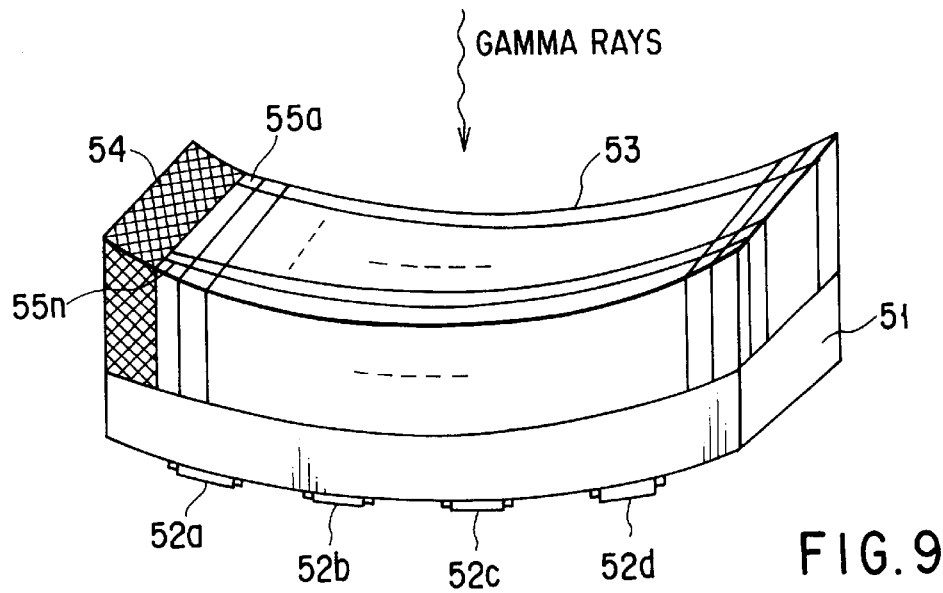
FIG. 9 is a view showing the construction of a detector module constructing the semiconductor radiation detector of this embodiment.

FIG. 9 is a view showing the construction of an integrally molded three-surface dense detector module. This three-surface dense detector module shown in FIG. 9 includes a substrate 51, a semiconductor cell array 53 formed on the surface of the substrate 51, a plurality of application specific integrated circuits (ASICs) 52a, 52b, 52c, and 52d (to be described below) formed on the opposite surface (back surface) of the substrate 51, and a mounting portion 54 for mounting the detector module on a fixing member.

The semiconductor cell array 53 has a plurality of semiconductor detecting elements 55a to 55n arrayed in a matrix manner. These semiconductor cells 55a to 55n have a one-to-one correspondence with pixels for reconstructing an image. "Three-surface dense" means that the dead space (dead zone) is very small. To realize a large field with this three-surface dense structure, one detector module is jointed to another detector module via three side surfaces, having no mounting portion, of four side surfaces adjacent to the incident surface of the detector module. The spatial resolution and detection sensitivity can be increased by minimizing the dead space. Even when a plurality of three-surface dense detector modules are jointed to construct a semiconductor radiation detector, individual semiconductor detecting elements are substantially equally spaced regardless of the existence of joint portions between the detector modules. Consequently, constant spatial resolution can be easily obtained.

The concave detector module as shown in FIG. 9 can also be constructed by using a scintillator instead of a semiconductor and mounting a plurality of photodiodes adjacent to the scintillator and parallel to each other.

Figure 10:
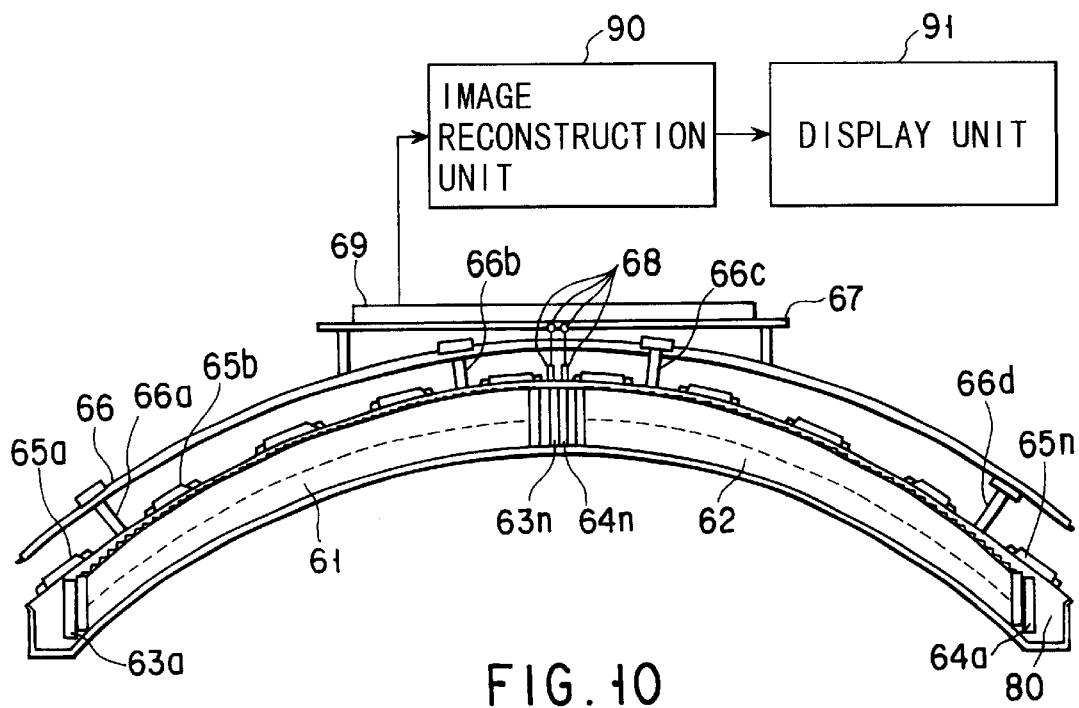
FIG. 10 is a view showing the assembly of two detector modules shown in FIG. 9.
Figure 11:
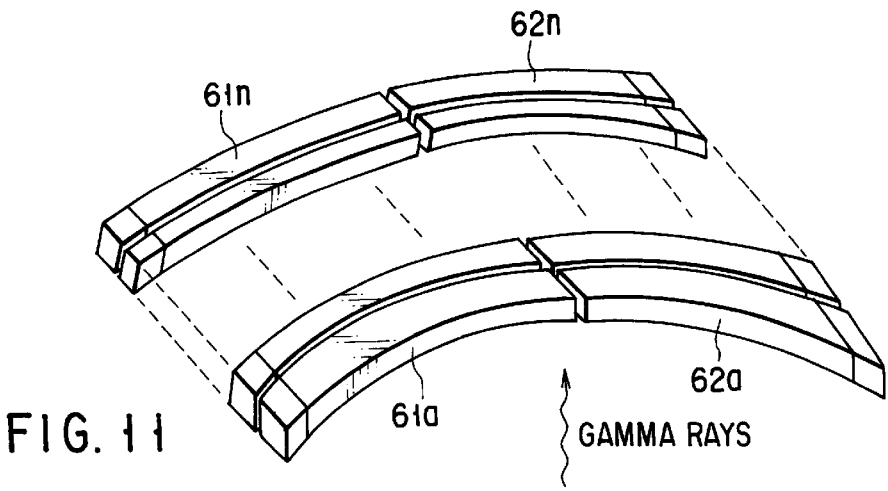
FIG. 11 is a view showing a large-field semiconductor radiation detector using the assembly of a plurality of detector modules shown in FIG. 9.
Figure 12:
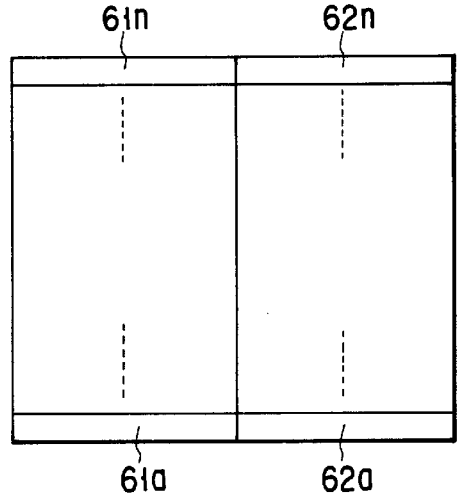
FIG. 12 is a plan view of the large-field semiconductor radiation detector shown in FIG. 11.

Referring to FIG. 10, two detector modules shown in FIG. 9 are vertically jointed. Also, as shown in FIGS. 11 and 12, a large-field two-dimensional semiconductor radiation detector including a plurality of detector modules 61a to 61n and 62a to 62n can be built by horizontally lining up a plurality of detector modules 61 and 62 shown in FIG. 10.

Figures 13, 14:
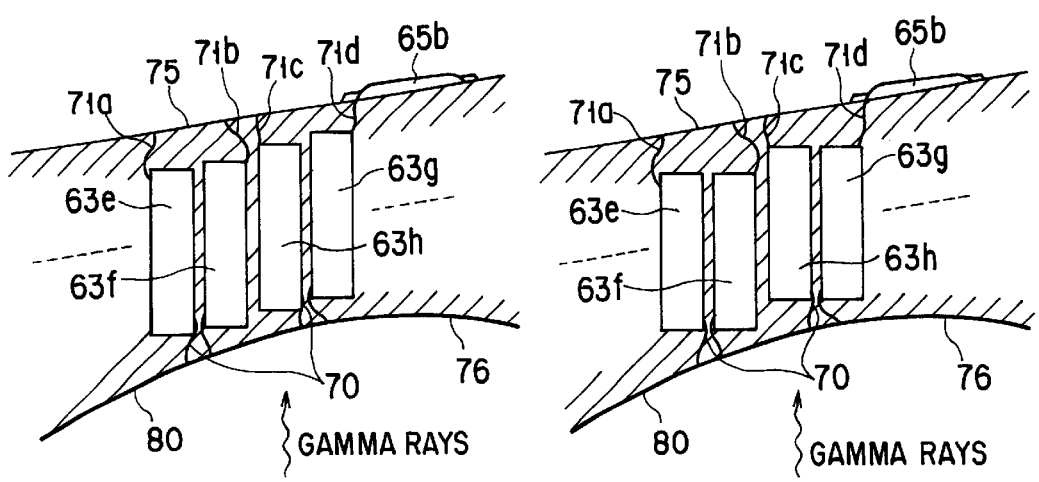
FIG. 13 is a view showing the internal structure of the detector module shown in FIG. 9.
FIG. 14 is a view showing another internal structure of the detector module shown in FIG. 9.

As shown in FIG. 13, a plurality of semiconductor cells 63a to 63n and 64a to 64n are integrally molded by a resin 80 or the like.

As shown in FIG. 10, the detector modules 61 and 62 have a signal wiring pattern for supplying output detection signals from the semiconductor cells 63a to 63n and 64a to 64n to a signal processor 69 and a high-voltage wiring pattern for applying a high voltage to the semiconductor cells 63a to 63n and 64a to 64n.

A plurality of application specific integrated circuits (ASICS) 65a to 65n composed of preamplifiers and read circuits for processing detection signals from the semiconductor cells 63a to 63n and 64a to 64n are arranged on the back surfaces (opposite to the incident surfaces) of the detector modules 61 and 62 so as not to extend from the incident surfaces of the semiconductor cells 63a to 63n and 64a to 64n.

The detector modules 61 and 62 are fixed to a copper plate 66 by screws and the like via projections 66a, 66b, 66c, and 66d. This copper plate 66 entirely covers the detector modules 61 and 62. The copper plate 66 is formed to have as large a ground surface as possible to electrically isolate (to shield digital signal noise) the signal processor 69 formed on a mother board 67 on the copper plate 66 and to dissipate heat generated from the ASICs 65a to 65n.

If the amount of heat from the ASICs 65a to 65n is large, it is possible to use an external heat dissipation structure by installing a forced cooling system (e.g., a Peltier cooler, heat pump, or fan, not shown) for dissipating heat transferred to the copper plate 66 via the projections 66a, 66b, 66c, and 66d to the outside.

A connector 68 electrically connects the ASICs 65a to 65n to the signal processor 69 on the mother board 67. The signal processor 69 processes output signals from the ASICs 65a to 65n and supplies its output to an image reconstruction unit 90. On the basis of this output, the image reconstruction unit 90 reconstructs an RI image. A display unit 91 displays the reconstructed RI image.

In this manner, it is possible to obtain a structure functioning as both a mechanical assembly and electrical wiring of the detector modules including the semiconductor cells.

As shown in FIG. 13, a plurality of semiconductor cells 63e, 63f, 63g, and 63h separated by thin walls (made of the resin 80), a voltage application electrode wiring pattern 70 as a common line for applying a high voltage to the semiconductor cells 63e, 63f, 63g, and 63h, and signal read electrode wiring patterns 71a, 71b, 71c, and 71d for extracting detection signals from the semiconductor cells 63e, 63f, 63g, and 63h are integrally molded by using the resin 80 or the like. In this structure, the voltage application electrode and the signal read electrodes are formed parallel to the gamma ray incident direction. Also, the incident surfaces of the semiconductor cells deviate from each other in the gamma ray incident direction to fit the curved surface (incident surface) of the detector module.

Since a parallel collimator is placed on a gamma ray incident surface 76, this gamma ray incident surface 76 is desirably a smooth curved surface. Additionally, since the thickness of the integrally formed detector modules is minimized to the extent to which necessary mechanical strength is ensured, the thickness of the detector modules 61a and 62a is set within the range of about 1.5 to 2.0 mm.

Furthermore, on a back surface 75 opposite to the gamma ray incident surface 76, the ASIC 65b and the like are mounted and various signal patterns are formed on this surface. So, this back surface 75 is not a curved surface but constructed of a plurality of plane surfaces.

As shown in FIG. 14, it is possible to align the incident surfaces of a plurality of adjacent semiconductor cells, e.g., a pair of semiconductor cells 63e and 63f (63g and 63h) and change the projection amount in units of these pairs.

Figure 15:
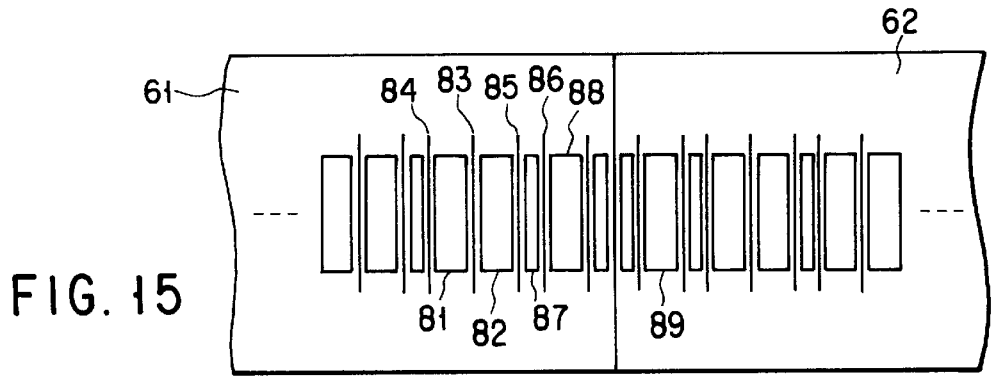
FIG. 15 is a view showing the internal structure of a connecting portion of two detector modules shown in FIG. 9.

As shown in FIG. 15, adjacent semiconductor cells 81 and 82 can share a voltage application electrode 83. Signal read electrodes 84, 85, and 86 are separately formed for the semiconductor detecting elements 81 and 82. An insulator 87 made of, e.g., a resin insulates the adjacent signal read electrodes 85 and 86 from each other.

In detector modules 61 and 62 as shown in FIG. 15, the gap width between the semiconductor cells in the connected portion is different from that in other portions. However, in the detector module 61, the distance between the centers of the semiconductor cells 81 and 82 adjacent to each other with the voltage application electrode 83 between them is set to be an integral multiple of the gap width between the adjacent semiconductor cells 81 and 82. The distance between the centers of semiconductor cells 88 and 89 is set to be an integral multiple of the gap width between the semiconductor cells 81 and 82. Additionally, a movement mechanism (not shown) moves the semiconductor radiation detector back and forth in a predetermined direction by a predetermined distance. Consequently, it is possible to eliminate image distortion resulting from mismatching between the actual spatial resolution and the resolution in image processing and obtain an image having predetermined resolution.

Figure 16:
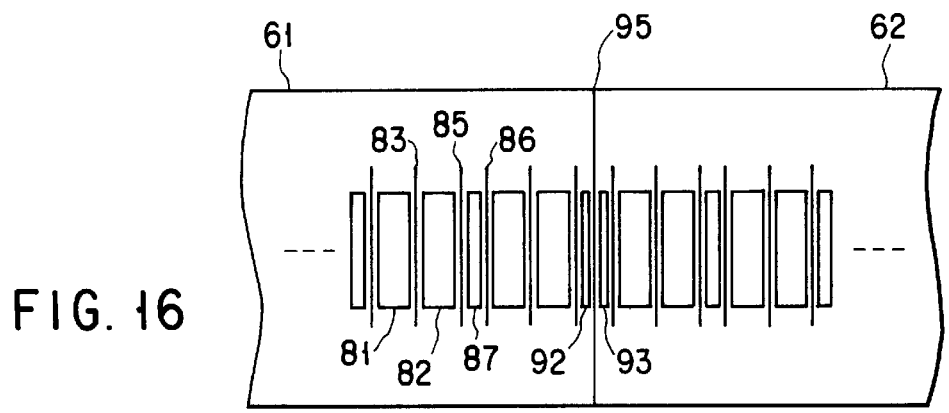
FIG. 16 is a view showing another internal structure of the connecting portion of two detector modules shown in FIG. 9.

As shown in FIG. 16, the thickness of insulators 92 and 93 formed near a junction surface 95 between detector modules is set to be about ½ the thickness of the insulator 87 between the signal read electrodes 85 and 86. Since the semiconductor cells 81 and 82 adjacent to each other with the voltage application electrode 83 between them are equally spaced, predetermined resolution can be obtained.

Figure 17:
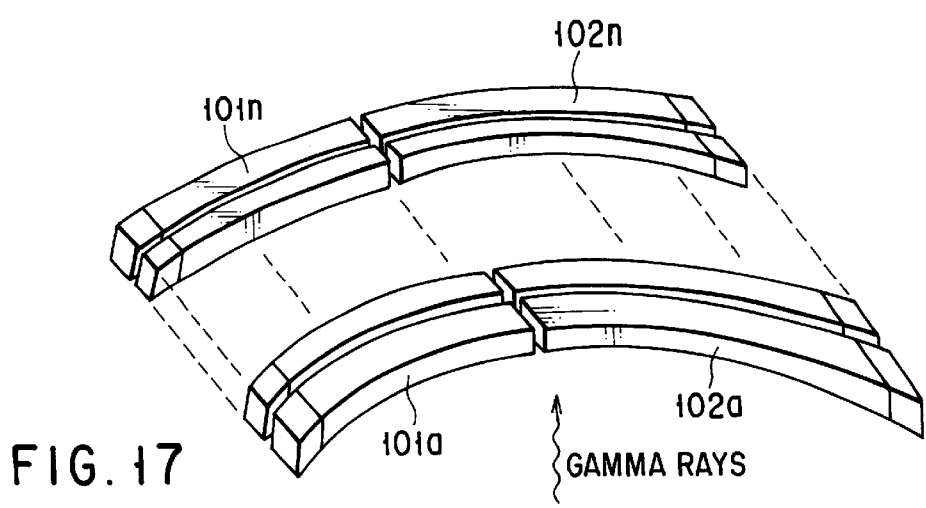
FIG. 17 is a view showing a modification of the large-field semiconductor radiation detector using the assembly of a plurality of detector modules shown in FIG. 9.

As shown in FIG. 17, a semiconductor radiation detector is constructed by combining two, left and right concave three-surface dense detector modules to form a concave shape with respect to a subject. In addition, a plurality of detector modules 101a to 101n and 102a to 102n are arranged in the direction normal to the paper to form a large field. The two, left and right detector modules shown in FIG. 11 have the same size. However, as in the semiconductor radiation detector shown in FIG. 17, the two, left and right detector modules can also have different sizes. Even with this construction, the incident surface of the semiconductor radiation detector can be moved close to a subject.

Figure 18:
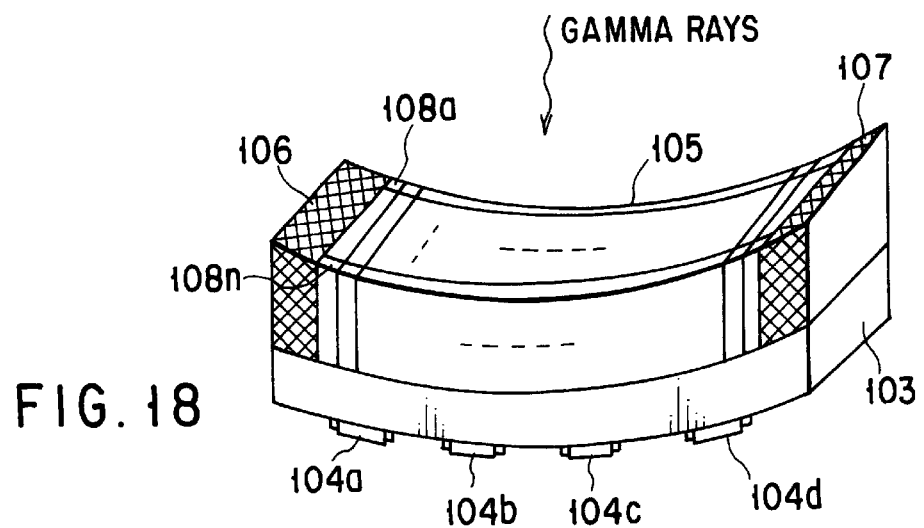
FIG. 18 is a view showing another construction of the detector module constructing the semiconductor radiation detector according to this embodiment.

As shown in FIG. 18, a curved two-surface dense detector module includes a substrate 103, a semiconductor detecting element array 105 formed on the surface of the substrate 103, a plurality of ASICs 104a, 104b, 104c, and 104d formed on the opposite surface (back surface) of the substrate 103, and mounting portions 106 and 107 formed on the two opposite side surfaces of the semiconductor cell array 105. These mounting portions 106 and 107 are used to mount this two-surface dense detector module onto a fixing member (not shown) to construct a semiconductor radiation detector. The semiconductor cell array 105 has a plurality of semiconductor cells 108a to 108n arrayed in a matrix manner.

"Two-surface dense" means that almost no dead space (dead zone) is formed and two side surfaces of one detector module can be jointed to side surfaces of other detector modules to thereby obtain a large-field semiconductor radiation detector. A "dead space" is a space smaller than a semiconductor cell usually corresponding to one pixel when a semiconductor radiation detector is viewed from the radiation incident surface. The smaller the dead space than a semiconductor cell, the more the spatial resolution and detection sensitivity can improve. Therefore, even when a semiconductor radiation detector is assembled by jointing a plurality of two-surface dense detector modules, individual semiconductor cells are substantially equally spaced regardless of the joint portions between the detector modules. So, predetermined spatial resolution can be readily obtained.

Even when this detector module is used, the concave detector module as shown in FIG. 17 can be constructed by using a scintillator instead of a semiconductor and arranging a plurality of, e.g., photodiodes adjacent to the scintillator and parallel to each other.

This two-surface dense detector module is formed to have a concave shape with respect to a subject without combining the three-surface dense detector module shown in FIG. 8.

Figure 19:
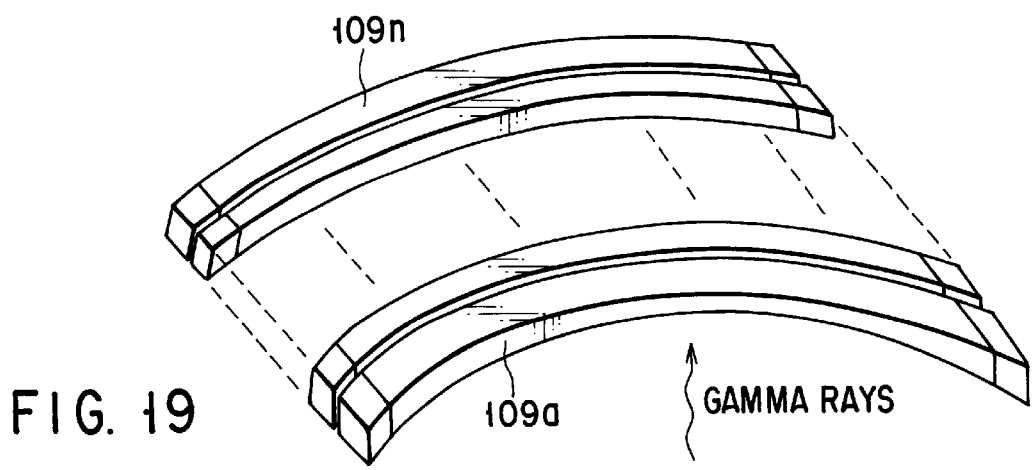
FIG. 19 is a view showing a large-field semiconductor radiation detector using the assembly of a plurality of detector modules shown in FIG. 18.

As shown in FIG. 19, a two-dimensional semiconductor radiation detector including a plurality of detector modules 109a to 109n by arranging a plurality of detector modules shown in FIG. 18 parallel to each other.

Figure 20:
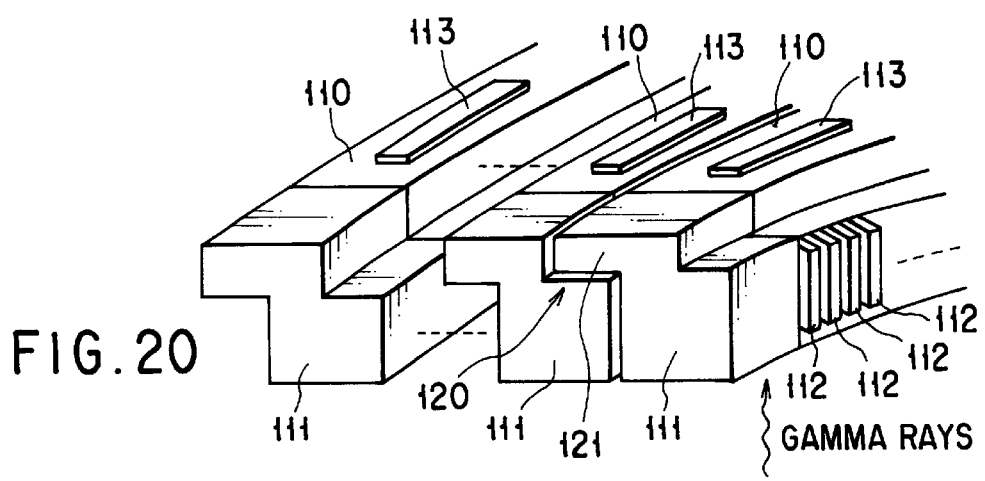
FIG. 20 is a view showing the structure of a connecting portion of the detector modules shown in FIG. 19.

As shown in FIG. 20, each of a plurality of detector modules 110 forming a large-field semiconductor radiation detector has a plurality of arrayed semiconductor cells 112, a mounting portion 111 for jointing to an adjacent detector module 110, and a connector 113 formed on the upper surface of the cell array. This connector 113 electrically connects to an ASIC (not shown) and transmits a detection signal from each semiconductor cell 112 to the ASIC. These detector modules 110 are molded into an L shape to allow easy jointing by using, e.g., a resin.

The semiconductor radiation detector shown in FIG. 20 is basically constructed by arranging a plurality of three-surface dense detector modules shown in FIG. 9 or a plurality of two-surface dense detector modules shown in FIG. 18 parallel to each other as shown in FIG. 11 or 19. However, each detector module 110 has a shape and internal structure different from those of the detector module shown in FIG. 9 or 18.

That is, each substantially rectangular detector module has a projection and step in its upper portion. This projection projects in a direction in which these detector modules line up to form a large field. Accordingly, the detector modules are assembled by placing a projection 121 of one detector module 110 on an upper step 120 of an adjacent detector module 110. This increases the joint area between adjacent detector modules compared to the case in which a large-field semiconductor radiation detector is constructed by arranging a plurality of detector modules 110 in a predetermined direction as shown in FIG. 11 or 19. Consequently, a firmer semiconductor radiation detector can be obtained.

Figure 21:
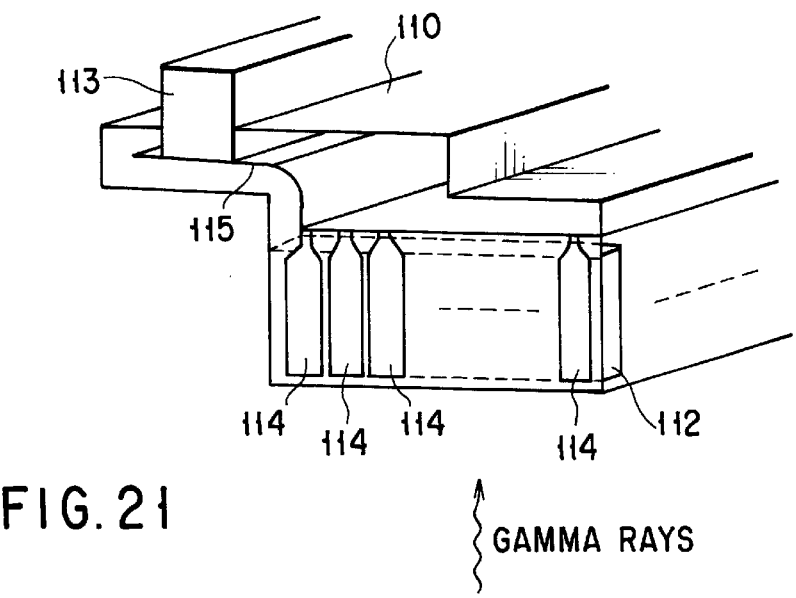
FIG. 21 is a cross-sectional view of FIG. 20.

The internal structure is shown in FIG. 21. That is, the detector module 110 has a flexible substrate 115 having a wiring pattern of conductor lines for electrodes (voltage application electrodes and signal read electrodes) 114. The use of the flexible substrate 115 having the wiring pattern facilitates connecting the electrodes 114 attached to the semiconductor cells 112 to the external ASIC connected via the connector 113.

A signal read portion can be formed on the flexible substrate to electrically connect directly to the ASIC, or the ASIC can be mounted on the surface of the flexible substrate, without forming the connector. This construction can simplify the internal structure of the detector module.

With the above construction, a concave semiconductor radiation detector which is difficult to realize with a monolithic semiconductor radiation detector can be formed relatively easily.

In this embodiment of the present invention, a parallel collimator and a fan beam collimator can have different thicknesses in different portions.

Applications when a semiconductor radiation detector constructed as above is used in various imaging scenes will be described below.

Figure 22:
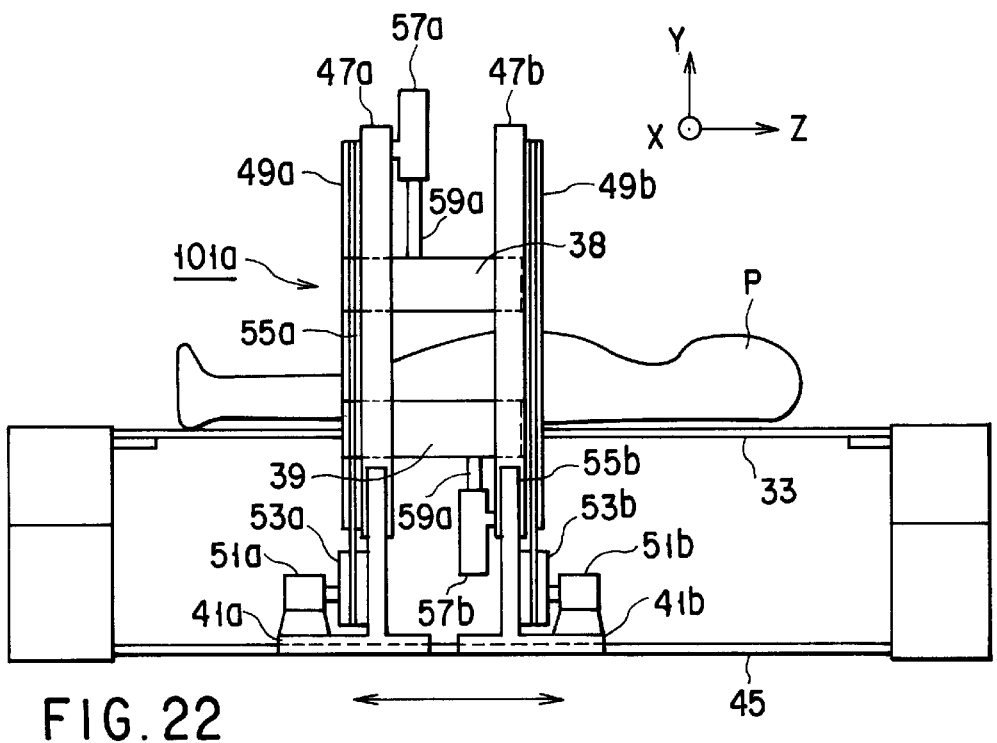
FIG. 22 is a side view showing the structure of a nuclear medicine diagnostic apparatus including two semiconductor radiation detectors according to this embodiment.
Figure 23:
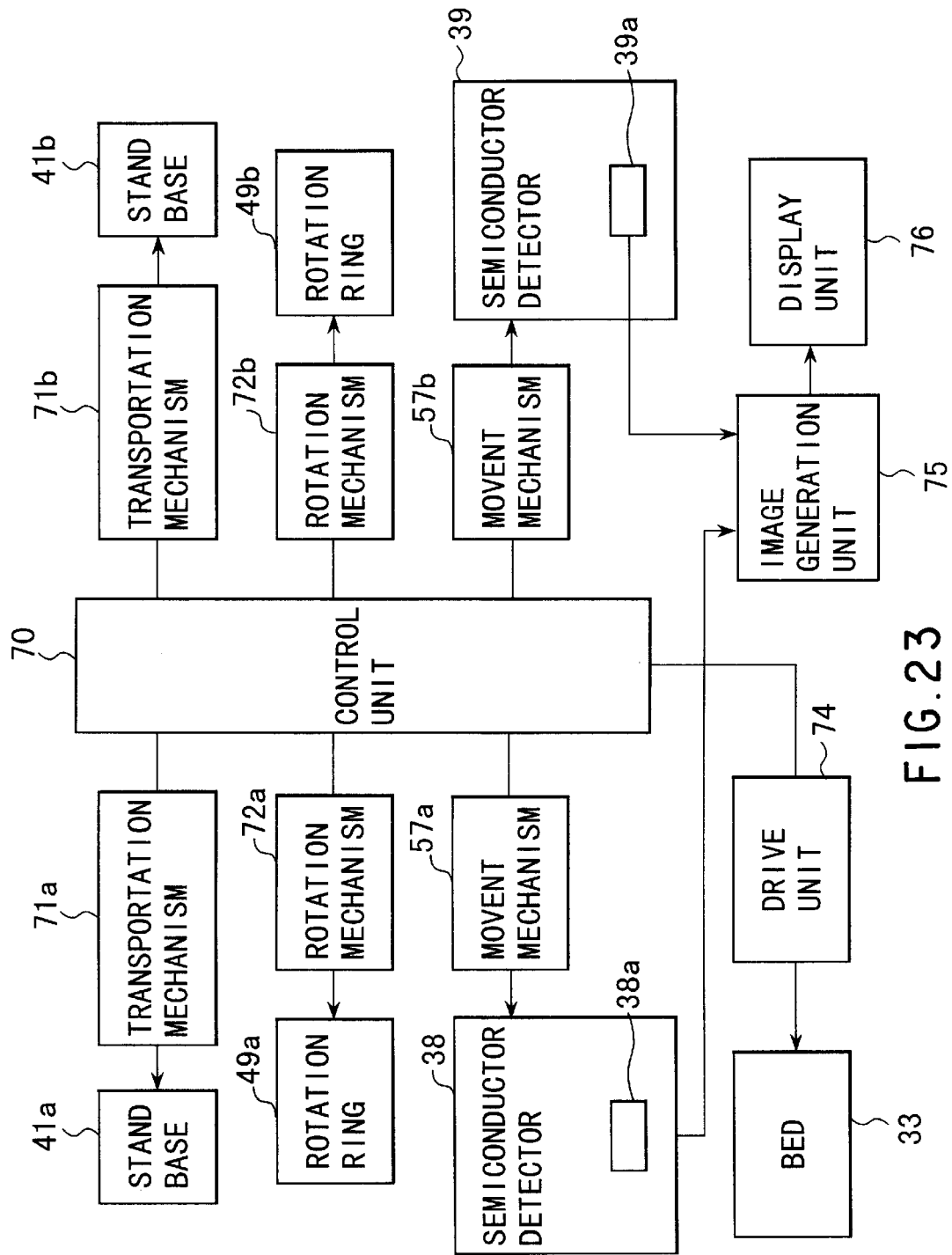
FIG. 23 is a block diagram showing the configuration of the nuclear medicine diagnostic apparatus shown in FIG. 22.

FIG. 22 shows the construction of a nuclear medicine diagnostic apparatus for achieving a wide variety of applications. FIG. 23 is a block diagram of this nuclear medicine diagnostic apparatus. This nuclear medicine diagnostic apparatus includes imaging systems a and b. Stand bases 41a and 41b are placed on transportation rails 45 and moved by transportation mechanisms 71a and 71b, respectively. These stand bases 41a and 41b have fixed rings 47a and 47b which rotatably support rotation rings 49a and 49b, respectively. Rotation mechanisms 72a and 72b rotate these rotation rings 49a and 49b, respectively. An arched semiconductor radiation detector 38 described above is attached to the rotation ring 49a via a three-dimensional movement mechanism 57a and a support arm 59a. Another arched semiconductor radiation detector 39 is attached to the rotation ring 49b via a three-dimensional movement mechanism 57b and a support arm 59b. In addition to cell arrays for detecting gamma rays from a subject P, the semiconductor radiation detectors 38 and 39 include signal processing units 38a and 38b for performing predetermined signal processing for the detection signals. A bed 33 on which the subject P lies down is moved vertically (in a Y direction) by a drive unit 74.

A control unit 70 controls the operations of all the transportation mechanisms 71a and 71b, the rotation mechanisms 72a and 72b, and the movement mechanisms 57a and 57b together. An image generation unit 75 generates an RI distribution on the basis of output signals from signal processing units 38a and 38b. A display unit 76 displays the RI distribution generated by the image generation unit 75.

The rotation mechanisms 72a and 72b are composed of drive motors 51a and 51b, drive gears 53a and 53b fitted on the drive shafts of the drive motors 51a and 51b, and belts 55a and 55b for interlocking the drive gears 53a and 53b and the rotation rings 49a and 49b, respectively.

In the above construction, the rotation mechanisms 72a and 72b rotate the rotation rings 49a and 49b under the control of the control unit 70. The movement mechanisms 57a and 57b vertically move the semiconductor radiation detectors 38 and 39 close to or away from the subject P, and also move the semiconductor radiation detectors 38 and 39 horizontally. Data is acquired while the semiconductor radiation detectors 38 and 39 move close to the subject P. To move the semiconductor radiation detectors 38 and 39 along the closest orbit to the subject P, the semiconductor radiation detectors 38 and 39 are actually moved before data acquisition to rehearse the closest orbit. In data acquisition, the control unit 70 controls the transportation units 71a and 71b, the rotation mechanisms 72a and 72b, the movement mechanisms 57a and 57b, and the drive unit 74 in accordance with the closest orbit information obtained by the rehearsal. As a consequence, the semiconductor radiation detectors 38 and 39 move on the closest orbit to the subject P.

A proximity switch formed on the incident surface of each of the semiconductor radiation detectors 38 and 39 to output a specific signal when the distance between the semiconductor radiation detector 38 or 39 and the subject comes close to the limit may make the closest orbit rehearsal unnecessary. In data acquisition, the movements of the semiconductor radiation detectors 38 and 39 are so controlled that these proximity switches do not continuously output the specific signal. This allows the semiconductor radiation detectors 38 and 39 to move substantially on the closest orbit.

Figure 24:
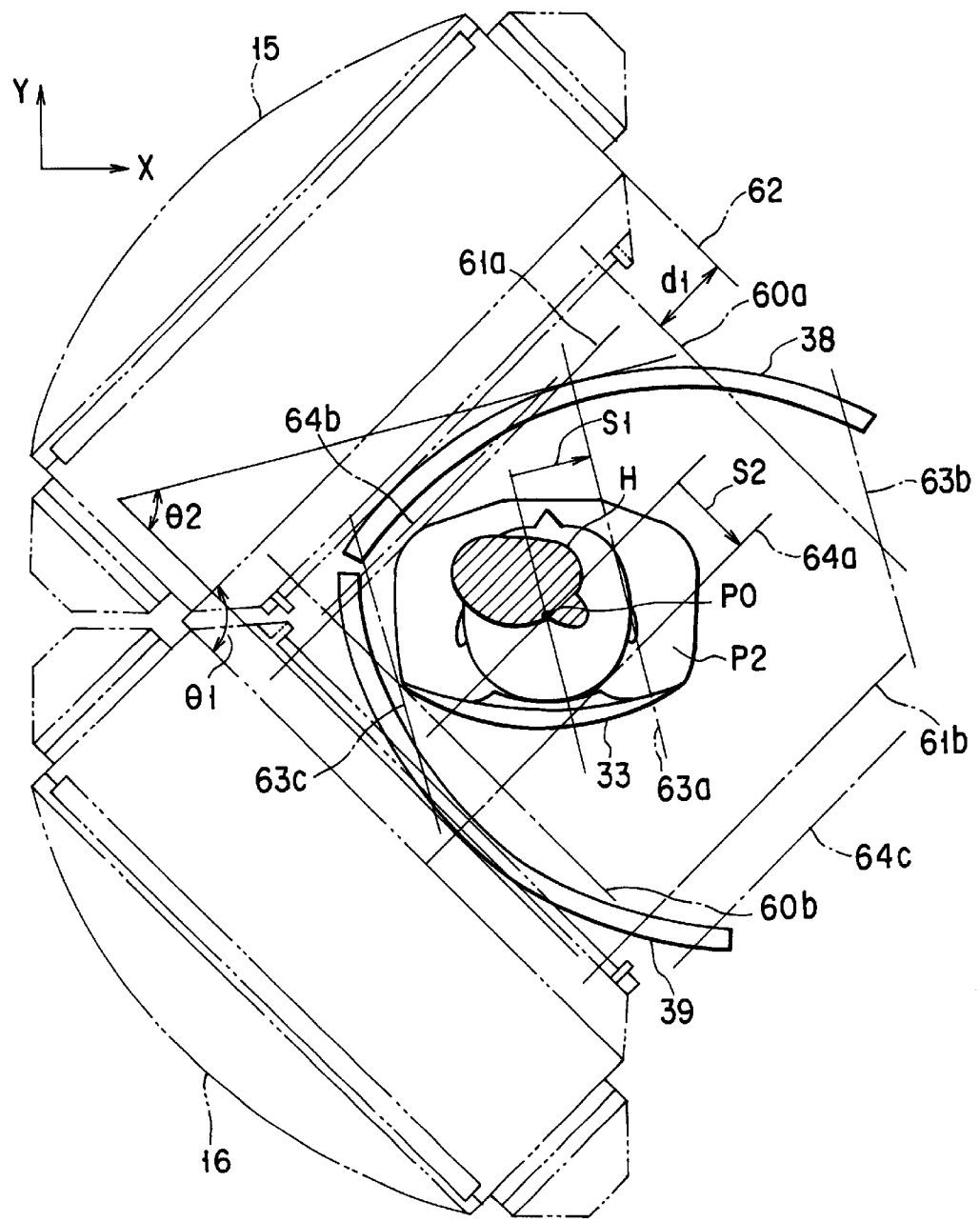
FIG. 24 is a view showing the arrangement of two semiconductor radiation detectors shown in FIG. 22 in a cardiac muscle SPECT operation.

The apparatus as shown in FIGS. 22 and 23 can flexibly cope with various examination situations. For example, in cardiac muscle SPECT imaging, the detectors 38 and 39 can be positioned as shown in FIG. 24. When conventional plane type semiconductor radiation detectors 15 and 16 are used, these semiconductor radiation detectors 15 and 16 are arranged 90° (θ1=90°) apart. A distance D1 is produced between a shield end 62 and effective field ends 60a, 60b, 61a, and 61b of the semiconductor radiation detectors 15 and 16. Hence, to move the semiconductor radiation detectors 15 and 16 closer to a heart H of a subject P2, complicated motions of the semiconductor radiation detectors 15 and 16 are required.

In this embodiment, however, the two concave semiconductor radiation detectors 38 and 39 can be so arranged that tangents to their centers intersect at an angle of 50° to 80°, e.g., 60°. Additionally, the semiconductor radiation detectors 38 and 39 are so designed as to have a width W of 40 to 65 cm, e.g., 60 cm and a bent depth D of 6 to 14 cm, e.g., 13 cm. Accordingly, all semiconductor cells in the semiconductor radiation detectors 38 and 39 can come very close to the heart H of the subject P2.

To keep the subject P2 inside the effective field, the semiconductor radiation detectors 38 and 39 are so positioned that field centers 63a and 63b align with a center P0 of the subject P2. When the semiconductor radiation detectors 38 and 39 are rotated around the subject P2 in this position, the semiconductor radiation detectors 38 and 39 sometimes move away from the heart H of the subject P2 depending on the rotation angle. In this embodiment, therefore, to prevent the semiconductor radiation detectors 38 and 39 from moving away from the heart H of the subject P2 depending on the rotation angle, the movement program code in the control unit 70 is so programmed that the field centers 63a and 64a of the semiconductor radiation detectors 38 and 39 shift from the subject center P0 at a specific rotation angle. Distances S1 and S2 the field centers 63a and 64a of the semiconductor radiation detectors 38 and 39 shift from the subject center P0 are 5 to 15 cm, e.g., 10 cm. This allows the semiconductor radiation detectors 38 and 39 to move closest to the heart H of the subject P2.

The semiconductor radiation detectors 38 and 39 can be moved closer to the subject P2 by combining the movement in the horizontal direction (X direction). According to calculations, the semiconductor radiation detectors 38 and 39 can come closer to the subject P2, in accordance with the body size of the subject P2, by about 40 to 50 mm on the average than the semiconductor radiation detector of the conventional Anger type gamma camera.

Additionally, in this embodiment the bed 33 need not be moved vertically (in the Y direction) to make the semiconductor radiation detectors approach the subject P2, unlike in the conventional systems. This gives the subject P2 no sense of anxiety. Also, it is possible to prevent deterioration of the image quality resulting from vibrations of the subject P2 by the vertical movement of the bed 33.

The conventional 90°-crossed semiconductor radiation detectors can acquire projection data of 180° by rotating 90°. In contrast, the two, 60°-crossed semiconductor radiation detectors 38 and 39 of this embodiment cannot acquire 180° projection data even by rotating 90°.

Figure 25:
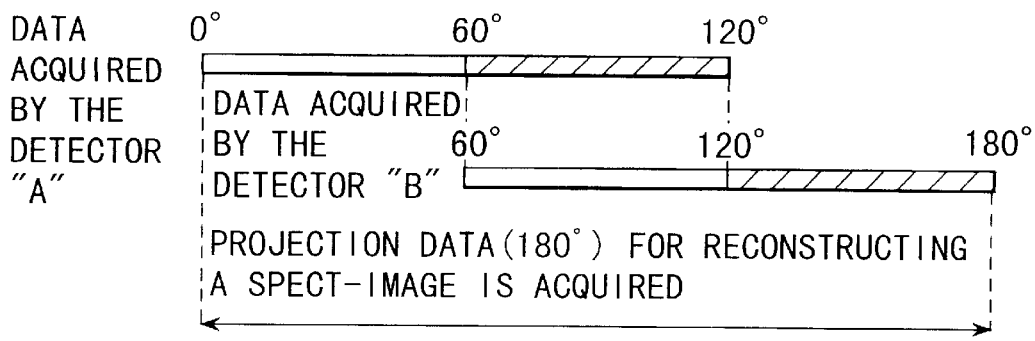
FIG. 25 is a view showing the data acquisition sequence of the two semiconductor radiation detectors in the cardiac muscle SPECT operation shown in FIG. 24.

As shown in FIG. 25, in this embodiment 180° projection data can be acquired by rotating two semiconductor radiation detectors A and B through 120°. That is, projection data of 0° to 120° is acquired when the two semiconductor radiation detectors A and B rotate from 0° to 60°. Projection data of 120° to 180° is acquired when the two semiconductor radiation detectors A and B rotate from 60° to 120°. If this is the case, only the semiconductor radiation detector B needs to be moved by taking account of the closest orbit to the subject. The reason for this is as follows. While the detector B is acquiring projection data of 120° to 180°, the other semiconductor radiation detector A can acquire projection data of 60° to 120°. However, the detector B has acquired this projection data of 60° to 120°, so the detector A need not acquire data. This obviates the need to drive the detector A close to the subject.

Consequently, during acquisition of projection data of 0° to 180°, the semiconductor radiation detector of this embodiment can come closer to the heart of a subject by about 40 to 50 mm than the conventional semiconductor radiation detectors. This allows the collimator arranged on the subject side of the incident surface of the semiconductor radiation detector to further approach the subject compared to the conventional collimators.

When a collimator having the same size as the semiconductor radiation detector of the conventional Anger type gamma camera is used in the semiconductor radiation detector of this embodiment, the projection data acquisition time is about 120/90°=1.33 times that of the conventional semiconductor radiation detector. However, the semiconductor radiation detector of this embodiment is located closer to a subject than the conventional semiconductor radiation detector and has higher positional resolution than that of the conventional semiconductor radiation detector. This combined effect achieves images having very high resolution. In other words, if a collimator is so designed as to have the same positional resolution as the conventional collimator, acquisition sensitivity twice as high as that of the conventional collimator can be obtained. Totally, therefore, acquisition sensitivity which is 2/1.33=1.5 times that of the conventional collimator or more can be obtained. This high sensitivity and the proximity effect that the semiconductor radiation detector has on a subject allow high-sensitivity cardiac muscle SPECT acquisition. Also, if acquisition aiming at high throughput is desirable, the acquisition time can be further shortened.

Additionally, when projection data from 0° to 180° is to be acquired, both of the two semiconductor radiation detectors are moved closest to a subject so that data obtained from the two semiconductor radiation detectors contributes to image reconstruction. Consequently, compared to the aforementioned case where only one of the two semiconductor radiation detectors is moved closest to a subject, it is possible to further increase the count used in image reconstruction and increase the acquisition sensitivity.

Figure 26:
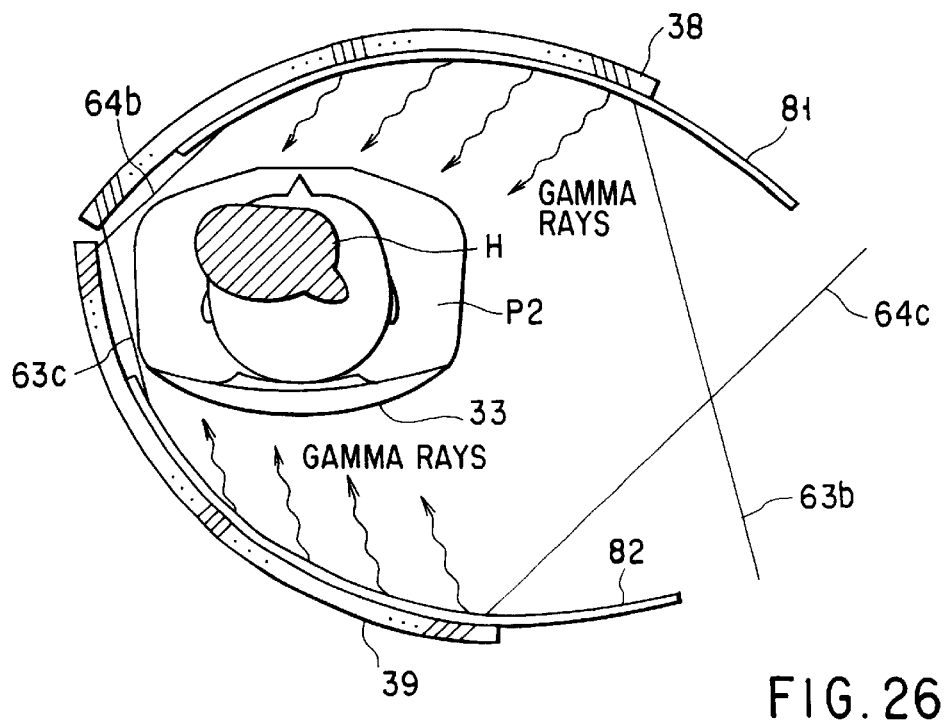
FIG. 26 is a view for explaining an absorption correction technique in the cardiac muscle SPECT operation shown in FIG. 24.

FIG. 26 is a view for explaining absorption correction applied to the 60° cardiac muscle SPECT acquisition described above. Plane radiation sources 81 and 82 for generating gamma rays are mounted on semiconductor radiation detectors 38 and 39 such that gamma rays perpendicularly strike the incident surfaces of semiconductor cells of the semiconductor radiation detectors 38 and 39. To perform emission acquisition operation and transmission acquisition operation at the same time, the plane radiation sources 81 and 82 are thinned to the extent to which the emission acquisition is not adversely affected. Also, the energy of gamma rays from the plane radiation sources 81 and 82 is made different from the energy of gamma rays from RIs injected into a subject. Accordingly, a semiconductor radiation detector having high energy resolution and very high count rate is optimum for a system like this.

When proper auxiliary guides (not shown) are formed on the incident surface sides of the semiconductor radiation detectors 38 and 39, the plane radiation sources 81 and 82 can be easily mounted on the semiconductor radiation detectors 38 and 39 along these auxiliary guides.

Figure 27:
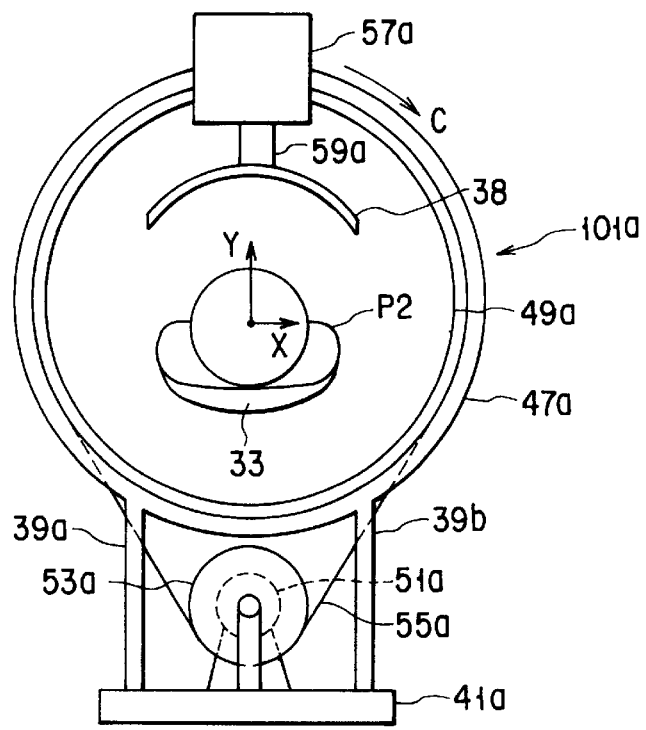
FIG. 27 is a side view showing the structure of a nuclear medicine diagnostic apparatus including one semiconductor radiation detector according to this embodiment.
Figure 28:
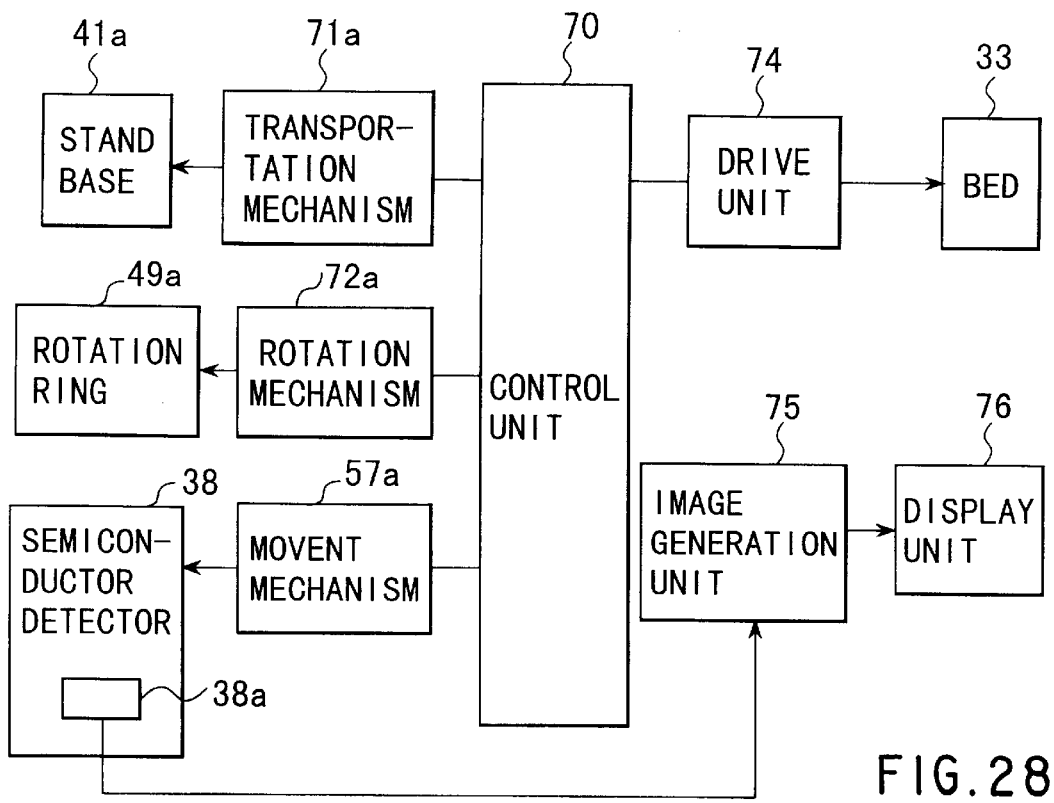
FIG. 28 is a block diagram showing the configuration of the nuclear medicine diagnostic apparatus shown in FIG. 27.

Next, the application of a concave semiconductor radiation detector as a single detector will be described below. FIG. 27 shows the structure of a nuclear medicine diagnostic apparatus including a single semiconductor radiation detector. FIG. 28 is a block diagram of this nuclear medicine diagnostic apparatus. A transportation mechanism 71a transports a stand base 41a. A fixed ring 47a is mounted on this stand base 41a via columns 39a and 39b. This fixed ring 47a supports a rotation ring 49a rotated by a rotation mechanism 72a. A semiconductor radiation detector 38 is mounted on the rotation ring 49a via a support arm 59a and a three-dimensional movement mechanism 57a. The semiconductor radiation detector 38 includes a signal processing unit 38a. A bed 33 on which a subject P2 lies down is moved vertically (in a Y direction) by a drive unit 74. A control unit 70 controls the operations of all the transportation mechanism 71a, the rotation mechanism 72a, the movement mechanism 57a, and the drive unit 74 together. An image generation unit 75 generates an RI distribution on the basis of an output from the signal processing unit 38a. A display unit 76 displays the RI distribution generated by the image generation unit 75.

The semiconductor radiation detector 38, the movement mechanism 57a, the rotation ring 49a, and the rotation mechanism 72a build a radiation detection system 101a.

The rotation mechanism 72a is constructed of a drive motor 51a, a drive gear 53a fitted on the drive shaft of the drive motor 51a, and a belt 55a extended between the drive gear 53a and the rotation ring 49a.

Under the control of the control unit 70, the rotation mechanism 72a rotates the rotation ring 49a, and the movement mechanism 57a moves the semiconductor radiation detector 38 in an arbitrary direction. With this combination of rotation and movement, the semiconductor radiation detector 38 acquires projection data of 180° while moving on the closest orbit to the subject P2.

To automatically move the semiconductor radiation detector 38 close to the subject P2 in projection data acquisition, the semiconductor radiation detector 38 is moved close to the subject P2 before the projection data acquisition. A storage unit (not shown) stores orbit information pertaining to this closest orbit of the semiconductor radiation detector 38. This orbit information allows the semiconductor radiation detector 38 to automatically move close to the subject P2 under the control of the control unit 70.

Alternatively, a proximity switch (not shown) is previously formed on the incident surface side of the semiconductor radiation detector 38. In projection data acquisition, the semiconductor radiation detector 38 can move in accordance with the proximity state with respect to the subject P2, that is based on output information from the proximity switch.

Figure 29:
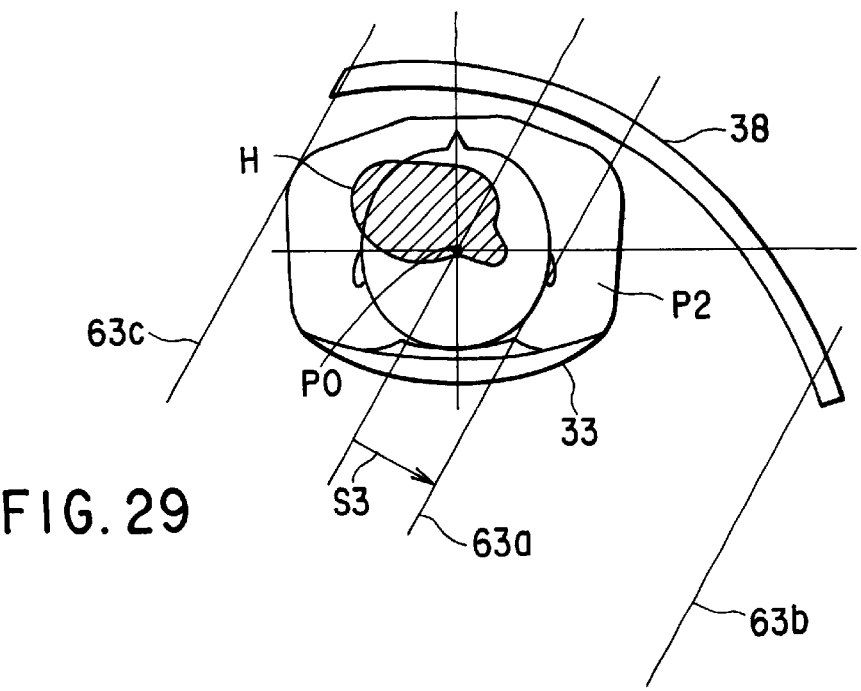
FIG. 29 is a view showing the arrangement of the semiconductor radiation detector shown in FIG. 27 in a cardiac muscle SPECT operation.
Figure 30A:
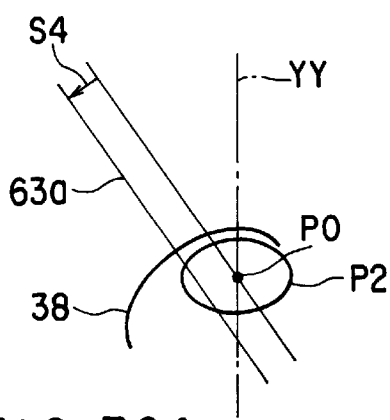
FIGS. 30A to 30C are views showing the cardiac muscle SPECT operation using the semiconductor radiation detector shown in FIG. 29.
Figure 30B:
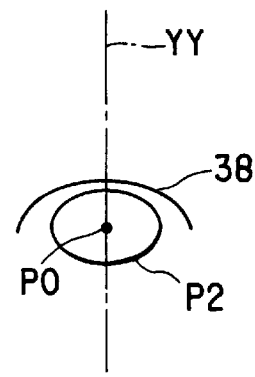
Figure 30C:
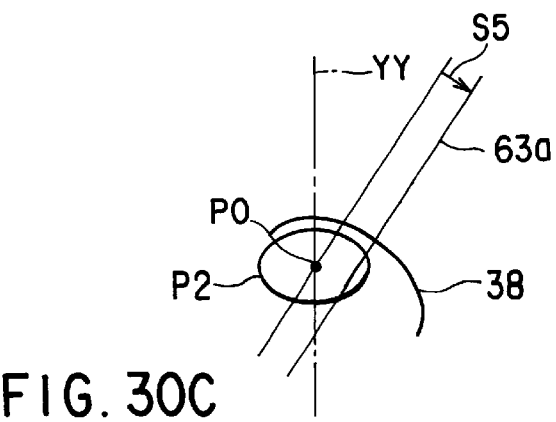

FIG. 29 shows the position of this single detector in cardiac muscle SPECT acquisition. The semiconductor radiation detector 38 is moved closest to the subject P2 as follows. That is, if, as shown in FIG. 30A, the semiconductor radiation detector 38 inclines leftward from a vertical line YY passing through a subject center P0 of the subject P2, a field center 63a of the semiconductor radiation detector 38 is shifted a predetermined distance S4 away from the vertical line YY. If the field center 63a of the semiconductor radiation detector 38 is on the vertical line YY as shown in FIG. 30B, the field center 63a is not shifted. If the semiconductor radiation detector 38 inclines rightward from the vertical line YY as shown in FIG. 30C, the field center 63a of the semiconductor radiation detector 38 is shifted a predetermined distance S5 away from the vertical line YY. The semiconductor radiation detector 38 is also moved away from or close to the subject P2 where necessary. These operations allow the semiconductor radiation detector 38 to move closest to the heart of the subject P2.

Figure 31:
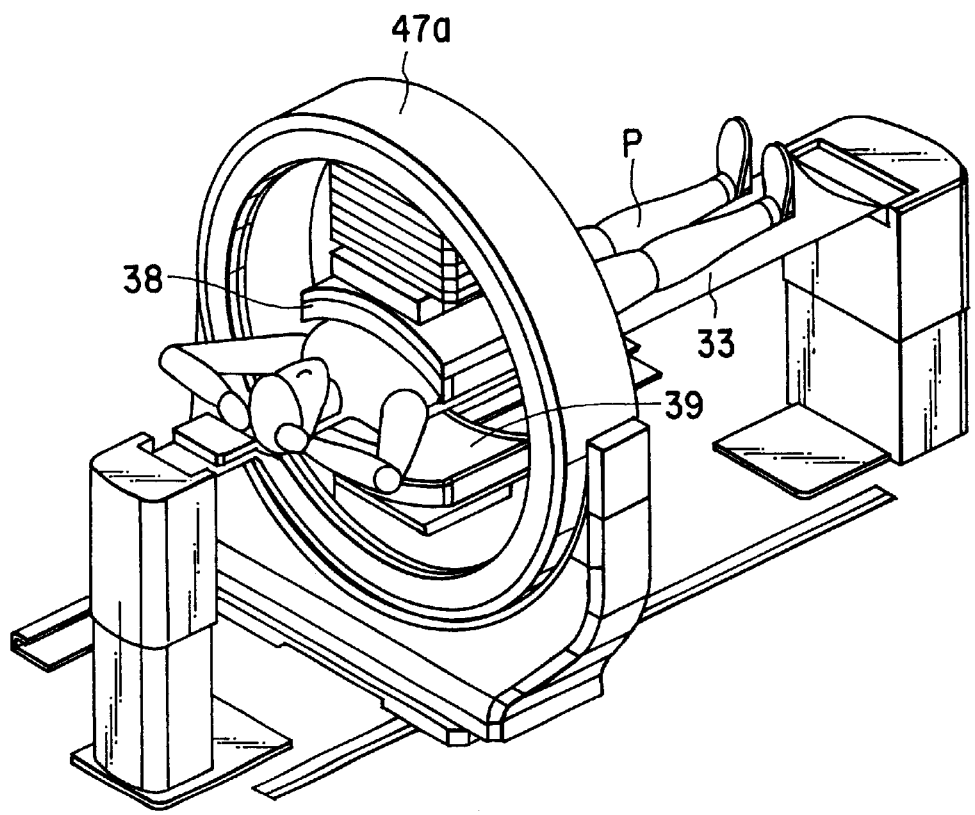
FIG. 31 is a view showing the structure of a nuclear medicine diagnostic apparatus having single gantry mounted two detectors according to this embodiment.

FIG. 31 shows the structure of a nuclear medicine diagnostic apparatus having single gantry mounted two detectors according to this embodiment. As showing FIG. 31, two detectors can be mounted on single gantry.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A semiconductor radiation detector comprising:
    a plurality of semiconductor cells for detecting radiation from a subject, said plurality of semiconductor cells being arrayed such that a cell array forms a concave shape and said plurality of semiconductor cells are parallel to each other;
    a plurality of voltage application electrodes formed in said plurality of semiconductor cells; and
    a plurality of signal read electrodes formed in said plurality of semiconductor cells.

2. A detector according to claim 1, wherein said plurality of semiconductor cells are arrayed such that said cell array is arched.

3. A detector according to claim 2, wherein each of said plurality of semiconductor cells projects from a right- or left-hand neighboring semiconductor cell, and the projection is shortest in a center and longest in a periphery.

4. A detector according to claim 2, wherein said plurality of semiconductor cells are divided into a plurality of groups, each semiconductor cell in each group projects from a right- or left-hand neighboring semiconductor cell, and the projection is shortest in a center and longest in a periphery.

5. A detector according to claim 2, wherein a semiconductor cell arranged in a center of said cell array is perpendicular to a tangent to the arch of said cell array.

6. A detector according to claim 2, wherein a semiconductor cell arranged in a center of said cell array is slanted to a tangent to the arch of said cell array.

7. A detector according to claim 1, wherein said plurality of semiconductor cells are arrayed such that said cell array forms a part of a polygon.

8. A detector according to claim 1, wherein said semiconductor cells are arranged in a line or in a matrix manner.

9. A detector according to claim 1, wherein said semiconductor cell has a predetermined thickness, and the thickness is a dimension of said semiconductor cell in a cell array direction.

10. A detector according to claim 1, wherein a thickness of semiconductor cells in a center and vicinity of said cell array is different from a thickness of semiconductor cells in a periphery and vicinity of said cell array, and the thickness is a dimension of said semiconductor cell in a cell array direction.

11. A detector according to claim 1, wherein a thickness of semiconductor cells in a periphery and vicinity of said cell array is larger than a thickness of semiconductor cells in a center and vicinity of said cell array, and the thickness is a dimension of said semiconductor cell in a cell array direction.

12. A detector according to claim 1, further comprising a parallel collimator attached to a gamma ray incident surface of said cell array and having a concave shape.

13. A detector according to claim 1, further comprising a fan beam collimator attached to a gamma ray incident surface of said cell array and having a concave shape.

14. A detector according to claim 1, further comprising a preprocessing circuit for preprocessing a detection signal from said semiconductor cell, said preprocessing circuit having a size equal to or smaller than a size of said cell array and arranged on a back surface of said cell array.

15. A detector according to claim 1, further comprising a plurality of modules constructing a plurality of portions of said cell array and one- or two-dimensionally jointed.

16. A detector according to claim 15, wherein each of said plurality of modules has a staircase shape so as to fit a neighboring module.

17. A detector according to claim 15, wherein each of said plurality of modules comprises a flexible substrate having a wiring pattern for connecting said plurality of signal read electrodes to an external signal processing circuit.

18. A detector according to claim 1, further comprising a movement mechanism for moving said cell array separately in a first direction in which said cell array moves close to and away from the subject and in a second direction perpendicular to the first direction.

19. A detector according to claim 18, further comprising a rotation mechanism for rotating said cell array around the subject, and a controller for controlling said rotation mechanism and said movement mechanism, said controller changing a position of said cell array with respect to the subject during rotation.

20. A semiconductor radiation detector comprising:
    a first cell array having a plurality of semiconductor cells for detecting radiation from a subject, a plurality of voltage application electrodes formed in said plurality of semiconductor cells, and a plurality of signal read electrodes formed in said plurality of semiconductor cells, said plurality of semiconductor cells being arrayed such that said first cell array forms a concave shape and said plurality of semiconductor cells are parallel to each other;
    a second cell array having a plurality of semiconductor cells for detecting radiation from the subject, a plurality of voltage application electrodes formed in said plurality of semiconductor cells, and a plurality of signal read electrodes formed in said plurality of semiconductor cells, said plurality of semiconductor cells being arrayed such that said second cell array forms a concave shape and said plurality of semiconductor cells are parallel to each other; and
    a structure for supporting said first and second cell arrays.

21. A detector according to claim 20, wherein said support structure opposes said first cell array to said second cell array with the subject therebetween.

22. A detector according to claim 20, wherein said support structure arranges said first cell array to make an angle excepting 180° with said second cell array.

23. A detector according to claim 20, further comprising a controller for controlling said support mechanism, said controller selectively arranging said first and second cell arrays in accordance with a plurality of arrangements including an arrangement in which said first cell array faces said second cell array and an arrangement in which said first cell array makes an angle excepting 180° with said second cell array.

24. A detector according to claim 20, further comprising a rotation mechanism for separately rotating said first and second cell arrays around the subject, and a controller for controlling said rotation mechanism and said support mechanism, said controller changing an arrangement of said first and second cell arrays during rotation.

25. A detector according to claim 20, further comprising a first fan beam collimator attached to said first cell array, and a second fan beam collimator attached to said second cell array, said support structure arranging said first cell array with respect to said second cell array such that a convergent point of said first fan beam collimator aligns itself with a convergent point of said second fan beam collimator.

26. A detector according to claim 20, further comprising a first radiation source attached to said first cell array, and a second radiation source attached to said second cell array, radiation emitted from said first radiation source being detected by said second cell array through the subject, and radiation emitted from said second radiation source being detected by said first cell array through the subject.

27. A nuclear medicine diagnostic apparatus comprising:
   a semiconductor radiation detector for detecting radiation from a subject administered a radioactive isotope;
   a unit for generating an internal distribution of the radioactive isotope on the basis of an output from said semiconductor radiation detector; and
   a unit for displaying the generated internal distribution,
   wherein said semiconductor radiation detector comprises:
      a plurality of semiconductor cells for detecting radiation from the subject, said plurality of semiconductor cells being arrayed such that a cell array forms a concave shape and said plurality of semiconductor cells are parallel to each other;
      a plurality of voltage application electrodes formed in said plurality of semiconductor cells; and
      a plurality of signal read electrodes formed in said plurality of semiconductor cells.

28. A nuclear medicine diagnostic apparatus comprising:
   a semiconductor radiation detector for detecting radiation from a subject administered a radioactive isotope;
   a unit for generating an internal distribution of the radioactive isotope on the basis of an output from said semiconductor radiation detector; and
   a unit for displaying the generated internal distribution,
   wherein said semiconductor radiation detector comprises:
      a first cell array having a plurality of semiconductor cells for detecting radiation from the subject, a plurality of voltage application electrodes formed in said plurality of semiconductor cells, and a plurality of signal read electrodes formed in said plurality of semiconductor cells, said plurality of semiconductor cells being arrayed such that said first cell array forms a concave shape and said plurality of semiconductor cells are parallel to each other;
      a second cell array having a plurality of semiconductor cells for detecting radiation from the subject, a plurality of voltage application electrodes formed in said plurality of semiconductor cells, and a plurality of signal read electrodes formed in said plurality of semiconductor cells, said plurality of semiconductor cells being arrayed such that said second cell array forms a concave shape and said plurality of semiconductor cells are parallel to each other; and
      a structure for supporting said first and second cell arrays.

29. A detector according to claim 28, wherein the angle between said first and second cell arrays is 50° to 80°.

* * * * *